United States Patent [19]
Bertram et al.

[11] Patent Number: 5,811,374
[45] Date of Patent: Sep. 22, 1998

[54] 3-ARYL-PYRROLIDINE-2,4-DIONE DERIVATIVES

[75] Inventors: Heinz-Jürgen Bertram, Holzminden; Reiner Fischer, Monheim; Bernd-Wieland Krüger, Bergisch Gladbach; Christoph Erdelen, Leichlingen; Klaus Lürssen; Robert R. Schmidt, both of Bergisch Gladbach; Hans-Joachim Santel, Leverkusen, all of Germany

[73] Assignee: Bayer Aktiengesellschaft, Leverkusen, Germany

[21] Appl. No.: 483,340

[22] Filed: Jun. 7, 1995

Related U.S. Application Data

[63] Continuation-in-part of Ser. No. 652,348, Feb. 7, 1991, abandoned.

[51] Int. Cl.⁶ .................... A01N 43/36; C07D 487/08
[52] U.S. Cl. .................... 504/246; 504/284; 504/218; 504/195; 546/183; 548/512; 540/302; 540/593; 540/476
[58] Field of Search .......................... 546/183; 548/512; 504/246, 284, 218, 195; 540/302, 593, 476

[56] References Cited

U.S. PATENT DOCUMENTS

| | | | |
|---|---|---|---|
| 4,094,985 | 6/1978 | Vladuchick | 514/373 |
| 4,531,969 | 7/1985 | Neslter | 504/316 |
| 4,550,205 | 10/1985 | Paerels | 564/166 |
| 4,943,640 | 7/1990 | Woo et al. | 548/551 |
| 4,985,063 | 1/1991 | Fischer | 514/183 |
| 5,045,560 | 9/1991 | Fischer et al. | 514/425 |
| 5,116,836 | 5/1992 | Fischer et al. | 514/224.2 |
| 5,288,874 | 2/1994 | Santel | 548/453 |

FOREIGN PATENT DOCUMENTS

| | | |
|---|---|---|
| 0 262 399 | 4/1988 | European Pat. Off. . |
| 0 355 599 | 2/1990 | European Pat. Off. . |
| 0 377 893 | 7/1990 | European Pat. Off. . |
| 0 415 211 | 3/1991 | European Pat. Off. . |
| 8 804 652 | 6/1988 | Japan . |

OTHER PUBLICATIONS

Liebigs Annalen Der Chemie, No. 5, 1985, pp. 1095–1098, Weinheim DE; R. Schmierer et al.: "Cyclisierung vin N–Acylalanin– und N–Acylglycinestern".

Chemical Abstracts 113(23) 204816g of JP 01 308 227 A2 By Heisei, Dec. 12, 1989.

Chemical Abstracts 109(13) 110249q of EP 262 399 A2 by Terao, Apr. 6, 1988.

Chemical Abstracts 113(21) 191153m of EP 355 599 A1 by Fischer, Feb. 28, 1990.

Chemical Abstracts 113(3) 23688w of DE 3 831 852 A1 by Fischer, Feb. 22, 1990.

*Primary Examiner*—C. Warren Ivy
*Assistant Examiner*—D. Margaret M. Mach
*Attorney, Agent, or Firm*—Sprung Kramer Schaefer & Briscoe

[57] ABSTRACT

New 3-arylpyrrolidine-2,4-dione derivatives of the formula (I):

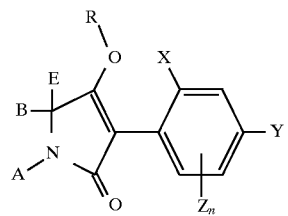

in which the variables A, B, E, R, X, Y, Z and n are set forth in the specification, are useful as insecticides, acaricides, and herbicides.

20 Claims, No Drawings

3-ARYL-PYRROLIDINE-2,4-DIONE DERIVATIVES

This is a Continuation-in-Part of application Ser. No. 07/652,348, filed Feb. 7, 1991, now abandoned.

The invention relates to new 3-aryl-pyrrolidine-2,4-dione derivatives, to a plurality of processes for their preparation, and to their use as insecticides, acaricides and herbicides.

Pharmaceutical properties have previously been described for 3-acyl-pyrrolidine-2,4-diones (S. Suzuki et. al. Chem. Pharm. Bull. 15 1120 (1967)). N-Phenyl-pyrrolidine-2,4-diones were furthermore synthesized by R. Schmierer and H. Mildenberger Liebigs Ann. Chem. 1985 1095. A biological activity of these compounds was not described.

EP-A 0,262,399 discloses compounds of a similar structure (3-aryl-pyrrolidine-2,4-diones), but no herbicidal, insecticidal or acaricidal action has been disclosed for these compounds.

New 3-arylpyrrolidine-2,4-dione derivatives have now been found, which are illustrated by the formula (I)

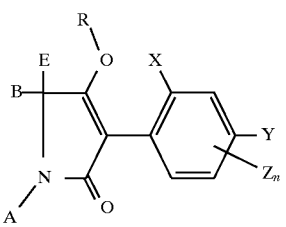

in which
- A represents optionally halogen-substituted alkyl, alkenyl, alkinyl, alkoxyalkyl, polyalkoxyalkyl, alkylthioalkyl or cycloalkyl which is optionally interrupted by hetero atoms, or represents arylalkyl which is optionally substituted by halogen, alkyl, halogenoalkyl, alkoxy or nitro,
- B and E independently of one another represent hydrogen, alkyl or alkoxyalkyl or
- A and B, together with the nitrogen or carbon atom to which they are bonded, form a cyclic ring which can be interrupted by hetero atoms or groups of hetero atoms,
- X represents alkyl, halogen or alkoxy,
- Y represents hydrogen, alkyl, halogen, alkoxy or halogenoalkyl,
- Z represents alkyl, halogen or alkoxy,
- n represents a number from 0–3,
- R represents the groups

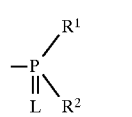 (a)

 (b)

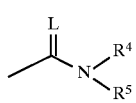 (c)

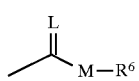 (d)

in which
L and M represent oxygen or sulphur, $R^1$, $R^2$ and $R^3$ independently of one another represent alkyl, alkoxy, alkylamino, dialkylamino, alkylthio, alkenylthio, alkinylthio or cycloalkylthio, each of which is optionally substituted by halogen, and represent phenyl, benzyl, phenoxy or phenylthio, each of which is optionally substituted, $R^4$ and $R^5$ independently of one another represent hydrogen, or represent alkyl, alkenyl, alkoxy or alkoxyalkyl, each of which is optionally substituted by halogen, or represent optionally substituted phenyl, or represent optionally substituted benzyl, or $R^4$ and $R^5$ together represent an alkylene radical which is optionally interrupted by oxygen, $R^6$ represents alkyl which is optionally substituted by halogen and which can be interrupted by oxygen, or represents phenyl which is optionally substituted by halogen, halogenoalkyl or alkoxy, or represents benzyl which is optionally substituted by halogen, halogenoalkyl, alkyl and alkoxy, or represents alkenyl or alkinyl, as well as the pure enantiomeric forms of compounds of the formula (I).

Taking into account the various meanings (a), (b), (c) and (d) of the group R of the general formula (I), the following main structures (Ia) to (Id) result:

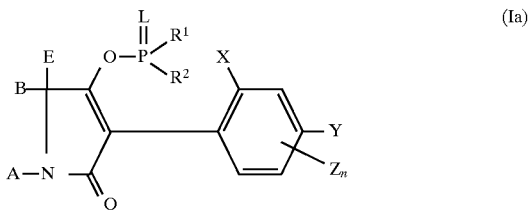 (Ia)

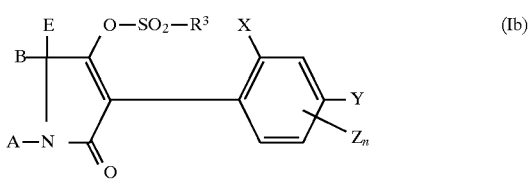 (Ib)

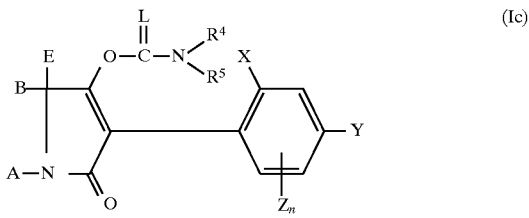 (Ic)

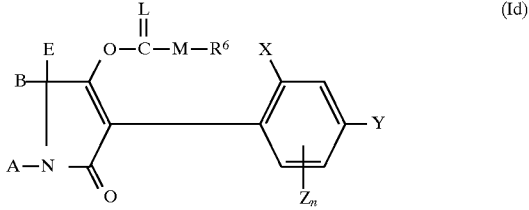 (Id)

where
A, B, E, L, M, X, Y, $Z_n$, $R^1$, $R^2$, $R^3$, $R^4$, $R^5$ and $R^6$ have the abovementioned meanings.

Furthermore, it has been found that 3-aryl-pyrrolidine-2,4-diones of the formula (Ia)

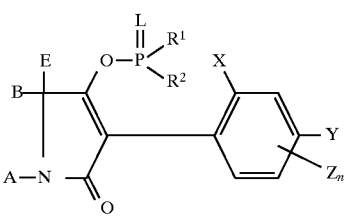 (Ia)

in which
A, B, E, L, X, Y, Z, $R^1$, $R^2$ and n have the abovementioned meaning, are obtained when A) 3-aryl-pyrrolidine-2,4-diones of the formula (II) or their enols

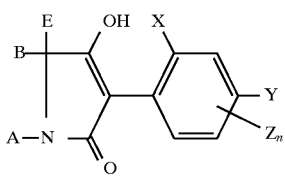 (II)

in which
A, B, E, X, Y, Z and n have the abovementioned meaning are reacted with phosphorus compounds of the general formula (III)

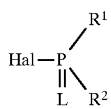 (III)

in which
L, $R^1$ and $R^2$ have the abovementioned meaning and Hal represents halogen, in particular chlorine and bromine, if appropriate in the presence of a diluent, if appropriate in the presence of an acid-binding agent and if appropriate in the presence of a phase transfer catalyst.

B) Furthermore, it has been found that compounds of the formula (Ib)

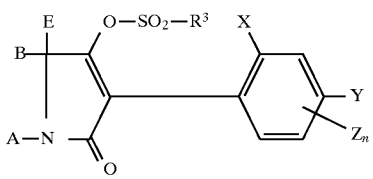 (Ib)

in which
A, B, E, X, Y, Z, $R^3$ and n have the abovementioned meaning are obtained when compounds of the formula (II)

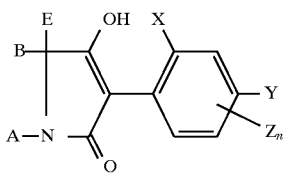 (II)

in which
A, B, E, X, Y, Z and n have the abovementioned meaning are reacted with sulphonyl chlorides of the general formula (IV)

 (IV)

in which
$R^3$ has the abovementioned meaning, if appropriate in the presence of a diluent and if appropriate in the presence of an acid-binding agent.

C) Furthermore, it has been found that compounds of the formula (Ic)

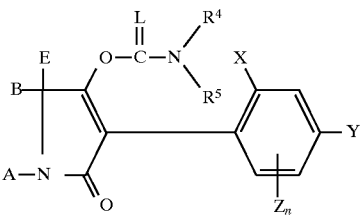 (Ic)

in which
A, B, E, L, X, Y, Z, $R^4$, $R^5$ and n have the abovementioned meaning are obtained when compounds of the formula (II)

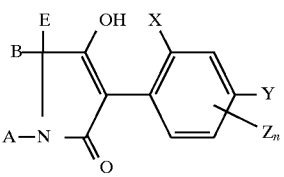 (II)

in which
A, B, E, X, Y, Z and n have the abovementioned meaning

α) are reacted with isocyanates of the general formula (V)

$R^4$—N=C=O (V)

in which
$R^4$ has the abovementioned meaning, if appropriate in the presence of a diluent and if appropriate in the presence of a catalyst, β) are reacted with carbamoyl chlorides or thiocarbamoyl chlorides of the general formula (VI)

 (VI)

in which
L, $R^4$ and $R^5$ have the abovementioned meaning, if appropriate in the presence of a diluent and if appropriate in the presence of an acid-binding agent.

D) Furthermore, it has been found that compounds of the formula (Id)

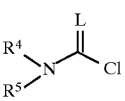 (Id)

in which
A, B, E, L, M, $R^6$, X, Y, Z and n have the abovementioned meaning are obtained when compounds of the formula (II)

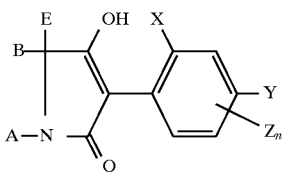

(ii)

in which
A, B, E, X, Y, Z and n have the abovementioned meaning are reacted

α) with chloromonothioformic esters, chloroformic thioesters or chlorodithioformic esters of the general formula VII

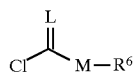

(VII)

in which
L, M and $R^6$ have the abovementioned meaning, if appropriate in the presence of a diluent and if appropriate in the presence of an acid-binding agent, or β) with carbon disulphide and subsequently with alkyl halides of the general formula VIII

   (VIII)

in which
$R^6$ has the abovementioned meaning and Hal represents chlorine, bromine or iodine.

E) Furthermore, it has been found that compounds of the formula (Ie)

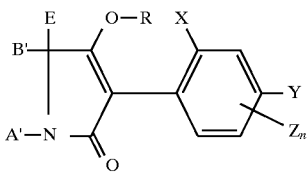

(Ie)

in which
R, X, Y, Z and n have the abovementioned meaning,
E represents hydrogen and
A' and B' together represent —$CH_2$—$CH_2$—SO—$CH_2$—, —$CH_2$—SO—$CH_2$—$CH_2$— or $CH_2$—SO—$CH_2$— are obtained when compounds of the formula (If)

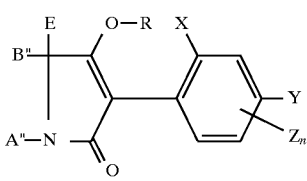

(If)

in which
R, X, Y, Z and n have the abovementioned meaning,
E represents hydrogen and
A" and B" together represent —$CH_2$—$CH_2$—S—$CH_2$—, —$CH_2$—S—$CH_2$—$CH_2$— or —$CH_2$—S—$CH_2$—, are reacted with approximately equimolar amounts of an oxidant, if appropriate in the presence of a diluent.

F) Furthermore, it has been found that compounds of the formula (Ig)

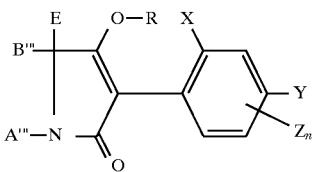

(Ig)

in which
R, X, Y, Z and n have the abovementioned meaning,
E represents hydrogen and
A''' and B''' together represent —$CH_2$—$CH_2$—$SO_2$—$CH_2$—, —$CH_2$—$SO_2$—$CH_2$—$CH_2$— or —$CH_2$—$SO_2$—$CH_2$— are obtained when compounds of the formula (If)

(If)

in which
R, X, Y, Z and n have the abovementioned meaning,
E represents hydrogen and
A" and B" together represent —$CH_2$—$CH_2$—S—$CH_2$—, —$CH_2$—S—$CH_2$—$CH_2$— or —$CH_2$—S—$CH_2$—, are reacted with at least twice the equimolar amounts of an oxidant, if appropriate in the presence of a diluent.

Surprisingly, it has been found that the new 3-arylpyrrolidine-2,4-dione derivatives of the formula (I) are distinguished by outstanding insecticidal, acaricidal and herbicidal actions.

Preferred 3-aryl-pyrrolidine-2,4-dione derivatives of the formula (I) are those in which A represents optionally halogen-substituted straight-chain or branched $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, $C_1$–$C_8$-polyalkoxy-$C_2$–$C_8$-alkyl, $C_1$–$C_{10}$–alkylthio-$C_2$–$C_8$-alkyl, cycloalkyl which has 3–8 ring atoms and which can be interrupted by oxygen and/or sulphur, or represents aryl-$C_1$–$C_6$-alkyl which is optionally substituted by halogen, $C_1$–$C_6$-alkyl-$C_1$–$C_6$-haloalkyl, $C_1$–$C_6$-alkoxy or nitro, B and E independently of one another represent hydrogen or straight-chain or branched $C_1$–$C_{12}$-alkyl or $C_1$–$C_8$-alkoxyalkyl, or A and B together with the nitrogen or carbon atom to which they are bonded form a 4 to 8-membered cyclic ring which can be interrupted by a sulphur atom or a sulphoxide or a sulphonyl group, X represents $C_1$–$C_6$-alkyl, halogen or $C_1$–$C_6$-alkoxy, Y represents hydrogen, $C_1$–$C_6$-alkyl, halogen, $C_1$–$C_6$-alkoxy or $C_1$–$C_3$-halogenoalkyl, Z represents $C_1$–$C_6$-alkyl, halogen or $C_1$–$C_6$-alkoxy, n represents a number from 0–3, R represents the groups

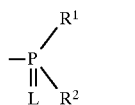  (a)

  (b)

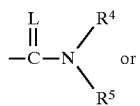  (c)

  (d)

in which

L and M in each case represent oxygen or sulphur, $R^1$, $R^2$ and $R^3$ independently of one another represent $C_1$–$C_8$-alkyl, $C_1$–$C_8$-alkoxy, $C_1$–$C_8$-alkylamino, di-($C_1$–$C_8$)-alkylamino, $C_1$–$C_8$-alkylthio, $C_2$–$C_5$-alkenylthio, $C_2$–$C_5$-alkinylthio or $C_3$–$C_7$-cycloalkylthio, each of which is optionally substituted by halogen, or represent phenyl, benzyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, $R^4$ and $R^5$ independently of one another represent $C_1$–$C_{20}$-alkyl, $C_1$–$C_{20}$-alkoxy, $C_2$–$C_8$-alkenyl or $C_1$–$C_{20}$-alkoxy-$C_1$–$C_{20}$-alkyl, each of which is optionally substituted by halogen, or represent phenyl which is optionally substituted by halogen, $C_1$–$C_{20}$-halogenoalkyl, $C_1$–$C_{20}$-alkyl or $C_1$–$C_{20}$-alkoxy, or represent benzyl which is optionally substituted by halogen, $C_1$–$C_{20}$-alkyl, $C_1$–$C_{20}$-halogenoalkyl or $C_1$–$C_{20}$-alkoxy, or together represent a $C_2$–$C_6$-alkylene ring which is optionally interrupted by oxygen, $R^6$ represents $C_1$–$C_{20}$-alkyl which is optionally substituted by halogen and which can be interrupted by oxygen, or represents phenyl which is optionally substituted by halogen, $C_1$–$C_{20}$-halogenoalkyl or $C_1$–$C_{20}$-alkoxy, or represents benzyl which is optionally substituted by halogen, $C_1$–$C_{20}$-halogenoalkyl or $C_1$–$C_{20}$-alkoxy, or represents $C_2$–$C_8$-alkenyl, or represents $C_2$–$C_5$-alkinyl, as well as the pure enantiomeric forms of compounds of the formula (I).

Particularly preferred compounds of the formula (I) are those in which

A represents optionally halogen-substituted straight-chain or branched $C_1$–$C_{10}$-alkyl, $C_3$–$C_6$-alkenyl, $C_3$–$C_6$-alkinyl, $C_1$–$C_8$-alkoxy-$C_2$–$C_8$-alkyl, $C_1$–$C_6$-polyalkoxy-$C_2$–$C_6$-alkyl, $C_1$–$C_8$-alkylthio-$C_2$–$C_6$-alkyl, cycloalkyl which has 3–7 ring atoms and which can be interrupted by 1–2 oxygen and/or sulphur atoms, or represents aryl-$C_1$–$C_4$-alkyl which is optionally substituted by halogen , $C_1$–$C_4$-alkyl, $C_1$–$C_4$-haloalkyl-$C_1$–$C_4$-alkoxy or nitro, B and E independently of one another represent hydrogen or straight-chain or branched $C_1$–$C_{10}$-alkyl or $C_1$–$C_6$-alkoxyalkyl, or A and B together with the nitrogen or carbon atom to which they are bonded form a 4-to 7-membered cycle which can be interrupted by a sulphur atom, or by a sulphoxide or sulphonyl group, X represents $C_1$–$C_4$-alkyl, halogen or $C_1$–$C_4$-alkoxy, Y represents hydrogen, $C_1$–$C_6$-alkyl, halogen, $C_1$–$C_4$-alkoxy or $C_1$–$C_2$-halogenoalkyl, Z represents $C_1$–$C_4$-alkyl, halogen or $C_1$–$C_4$-alkoxy, n represents a number from 0–3, R represents the groups

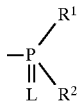  (a)

  (b)

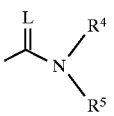  (c)

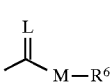  (d)

in which

L and M in each case represent oxygen or sulphur, $R^1$, $R^2$ and $R^3$ independently of one another represent $C_1$–$C_6$-alkyl, $C_1$–$C_6$-alkoxy, $C_1$–$C_6$-alkylamino, di-($C_1$–$C_6$)-alkylamino, $C_1$–$C_6$-alkylthio, $C_3$–$C_4$-alkenylthio, $C_2$–$C_4$-alkinylthio or $C_3$–$C_6$-cycloalkylthio, each of which is optionally substituted by halogen, or represent phenyl, benzyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl, $R^4$ and $R^5$ independently of one another represent $C_1$–$C_{20}$-alkyl, $C_1$–$C_{20}$-alkoxy, $C_2$–$C_8$-alkenyl or $C_1$–$C_{20}$-alkoxy-$C_1$–$C_{20}$-alkyl, each of which is optionally substituted by halogen, or represent phenyl which is optionally substituted by halogen, $C_1$–$C_5$-halogenoalkyl, $C_1$–$C_5$-alkyl or $C_1$–$C_5$-alkoxy, or represent benzyl which is optionally substituted by halogen, $C_1$–$C_5$-alkyl, $C_1$–$C_5$-halogenoalkyl or $C_1$–$C_5$-alkoxy, $R^6$ represents $C_1$–$C_{20}$-alkyl which is optionally substituted by halogen and which can be interrupted by oxygen, or represents phenyl which is optionally substituted by halogen, $C_1$–$C_5$-halogenoalkyl or $C_1$–$C_5$-alkoxy, or represents benzyl which is optionally substituted by halogen, $C_1$–$C_5$-halogenoalkyl or $C_1$–$C_5$-alkoxy, as well as the pure enantiomeric forms of compounds of the formula (I).

Particularly preferred compounds of the formula (I) are those in which

A represents optionally halogen-substituted straight-chain or branched $C_1$–$C_8$-alkyl, $C_3$–$C_4$-alkenyl, $C_3$–$C_4$-alkinyl, $C_1$–$C_6$-alkoxy-$C_2$–$C_4$-alkyl, $C_1$–$C_4$-polyalkoxy-$C_2$–$C_4$-alkyl, $C_1$–$C_6$-alkylthio-$C_2$–$C_4$-alkyl, cycloalkyl which has 3–6 ring atoms and which can be interrupted by 1–2 oxygen and/or sulphur atoms, or represents aryl-$C_1$–$C_3$-alkyl which is optionally substituted by fluorine, chlorine, bromine, methyl, ethyl, propyl, iso-propyl, methoxy, ethoxy, trifluoromethyl or nitro, B and E independently of one another represent hydrogen or straight-chain or branched $C_1$–$C_8$-alkyl or $C_1$–$C_4$-alkoxyalkyl, or A and B together with the nitrogen or carbon atom to which they are bonded form a 5-6-membered cyclic ring which can be interrupted by a sulphur atom or by a sulphoxide or sulphonyl group, X represents methyl, ethyl, propyl, i-propyl, fluorine, chlorine, bromine, methoxy or ethoxy, Y represents hydrogen, methyl, ethyl, propyl, i-propyl, butyl, i-butyl, tert.-butyl, fluorine, chlorine, bromine, methoxy, ethoxy or trifluoromethyl, Z represents methyl, ethyl, i-propyl, butyl, i-butyl, tert.-butyl, fluorine, chlorine, bromine, methoxy or ethoxy, n represents a number from 0–3, R represents the groups

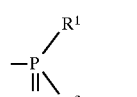 (a)

 (b)

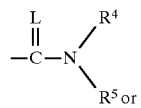 (c)

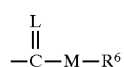 (d)

in which

L and M in each case represent oxygen or sulphur, $R^1$, $R^2$ and $R^3$ independently of one another represent $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio, each of which is optionally substituted by fluorine or chlorine, or represent phenyl, benzyl, phenoxy or phenylthio, each of which is optionally substituted by fluorine, chlorine, bromine, nitro, cyano, $C_1$–$C_2$-alkoxy, $C_1$–$C_4$-fluoroalkoxy, $C_1$–$C_2$-chloroalkoxy, $C_1$–$C_2$-alkylthio, $C_1$–$C_2$-fluoroalkylthio, $C_1$–$C_2$-chloroalkylthio or $C_1$–$C_3$-alkyl, $R^4$ and $R^5$ independently of one another represent $C_1$–$C_{10}$-alkyl, $C_1$–$C_{10}$-alkoxy or $C_1$–$C_{10}$-alkoxy-($C_1$–$C_{10}$)alkyl, each of which is optionally substituted by fluorine, chlorine or bromine, or represent phenyl which is optionally substituted by fluorine, chlorine, bromine, $C_1$–$C_{20}$-halogenoalkyl, $C_1$–$C_{20}$-alkyl or $C_1$–$C_4$-alkoxy, or represent benzyl which is optionally substituted by fluorine, chlorine, bromine, $C_1$–$C_4$-alkyl, $C_1$–$C_4$-halogenoalkyl or $C_1$–$C_4$-alkoxy, $R^6$ represents $C_1$–$C_{10}$-alkyl which is optionally substituted by fluorine, chlorine or bromine and which can be interrupted by oxygen, or represents phenyl which is optionally substituted by fluorine, chlorine, bromine, $C_1$–$C_4$-halogenoalkyl or $C_1$–$C_4$-alkoxy, or represents benzyl which is optionally substituted by fluorine, chlorine, bromine, $C_1$–$C_4$-halogenoalkyl or $C_1$–$C_4$-alkoxy, as well as the pure enantiomeric forms of compounds of the formula (I).

If, according to process (A), 3-(2,4,6-trimethylphenyl)-1,5-trimethylene-2,4-pyrrolidine-dione and 2,2,2-trifluoroethyl methanethio-chlorophosphonate are used as starting materials, the course of the reaction can be illustrated by the following equation:

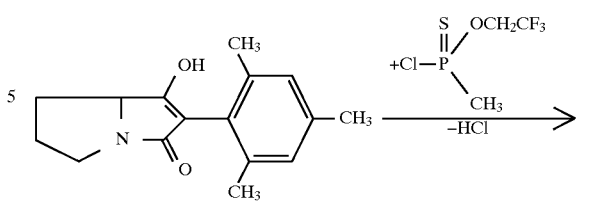

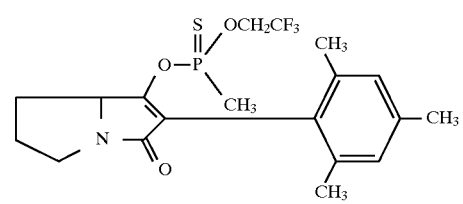

If, according to process (B), 3-(2,4,6-trimethylphenyl)-1,5-trimethylene-2,4-pyrrolidine-dione and methanesulphonyl chloride are used as starting materials, the course of the reaction can be illustrated by the following equation:

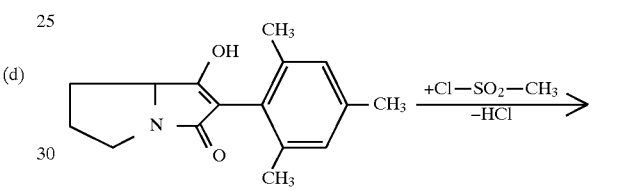

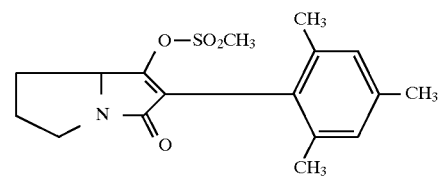

If, according to process ($C_\alpha$) 3-(2,4,6-trimethylphenyl)-1,5-trimethylene-2,4-pyrrolidine-dione and ethyl isocyanate are used as starting materials, the course of the reaction can be illustrated by the following equation:

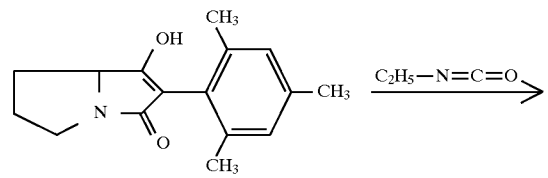

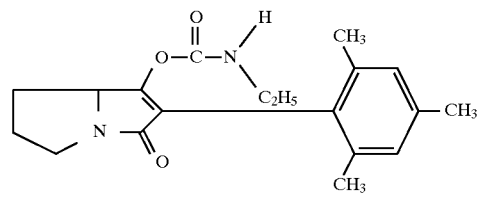

If, according to process ($C_\beta$), 3-(2,4,6-trimethylphenyl)-1,5-trimethylene-2,4-pyrrolidine-dione and dimethylcarbamoyl chloride are used as starting materials, the course of the reaction can be illustrated as follows:

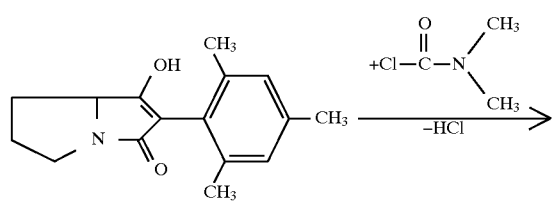

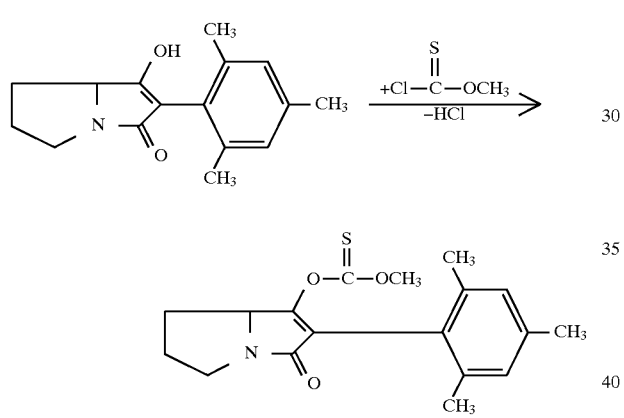

If, according to process (D$_\alpha$), 3-(2,4,6-trimethylphenyl)-1,5-tetramethylene-2,4-pyrrolidine-dione and methyl chloromonothioformate are used as starting materials, the course of the reaction can be illustrated as follows:

If, according to process (D$_\beta$), 3-(2,4,6-trimethylphenyl)-1,5-tetramethylene-2,4-pyrrolidine-dione, carbon disulphide and methyl iodide are used as starting components, the course of the reaction can be illustrated as follows:

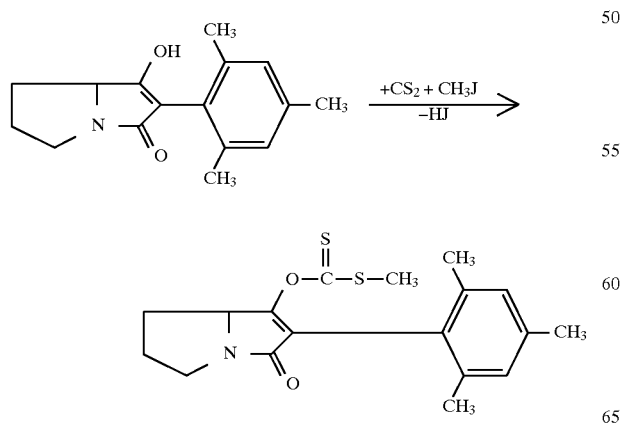

Process (E) can be illustrated as follows:

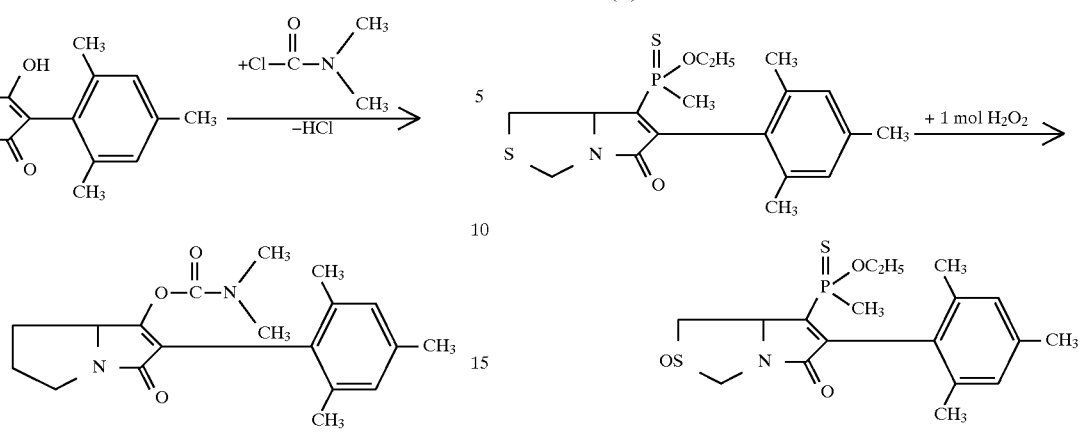

Process (F) can be illustrated as follows:

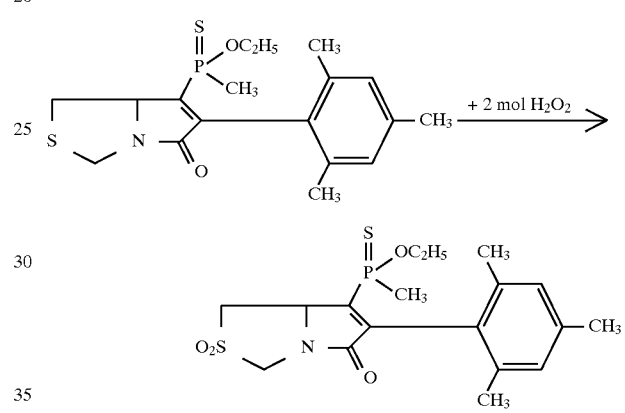

The compounds of the formula (II)

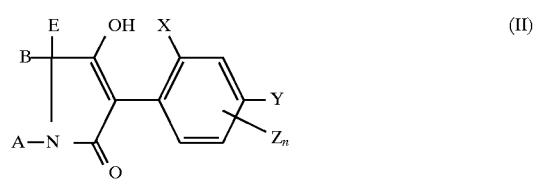

in which

A, B, E, X, Y, Z and n have the abovementioned meaning and which are required as starting substances in the above processes (A)–(D), are new. For example, compounds of the formula (II) are obtained when N-acylamino acid esters of the formula (IX)

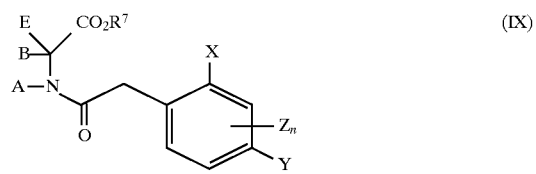

in which
A, B, E, X, Y, Z and n have the abovementioned meaning and
$R^7$ represents alkyl are subjected to intramolecular condensation in the presence of a diluent and in the presence of a base.

Some of the compounds of the formula (IX)

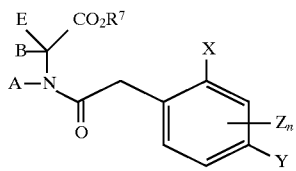
(IX)

in which
A, B, E, X, Y, Z, n and $R^7$ have the abovementioned meaning and which are required as starting substances in the above process, are known or can be prepared in a simple manner by methods which are known in principle. For example, acyl-amino acid esters of the formula (II) are obtained when
a) amino acid esters of the formula (X)

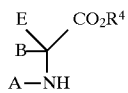
(X)

in which
$R^4$ represents hydrogen (Xa) and alkyl (Xb) and
A, B and E have the abovementioned meaning are acylated with phenylacetic halides of the formula (XI)

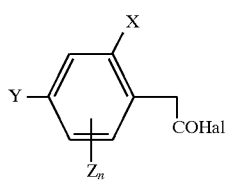
(XI)

in which
X, Y, Z and n have the abovementioned meaning and Hal represents chlorine or bromine (Chem. Reviews 52 237–416 (1953));
or when acylamino acids of the formula (IIa)

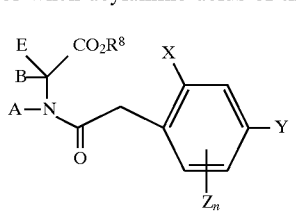
(IIa)

in which
A, B, E, X, Y, Z and n have the abovementioned meaning and
$R^8$ represents hydrogen are esterified (Chem. Ind. (London) 1568 (1968).

To obtain compounds of the structure (Ia), 1 to 2, preferably 1 to 1.3, moles of the phosphorus compound of the formula (III) are reacted per mole of the compound (II) in preparation process A) at temperatures of between −40° and 150° C., preferably between −10° and 110° C.

Suitable diluents which are optionally added are all inert, polar organic solvents, such as ethers, amides, nitrites, alcohols, sulphides, sulphones, sulphoxides etc.

Diluents which are preferably employed are acetonitrile, dimethyl sulphoxide, tetrahydrofuran, dimethylformamide and dimethyl sulphide.

Suitable acid-binding agents which are optionally added are customary inorganic or organic bases, such as hydroxides or carbonates. Examples which may be mentioned are sodium hydroxide, sodium carbonate, potassium carbonate and pyridine.

The reaction can be carried out at atmospheric pressure or under elevated pressure, preferably at atmospheric pressure. The products are worked up by methods which are customary in organic chemistry. The end products obtained are preferably purified by crystallization, chromatographic purification or by so-called "incipient distillation", that is to say, removal of the volatile constituents in vacuo.

Approximately 1 mole of sulphonyl chloride (IV) is reacted per mole of starting compound of the formula (II) in preparation process B), at 0° to 150° C., preferably at 20° to 70° C.

Suitable diluents which can optionally be added are all inert, polar organic solvents, such as ethers, amides, nitrites, alcohols, sulphones and sulphoxides.

Diluents which are preferably employed are dimethyl sulphoxide, tetrahydrofuran, dimethylformamide and dimethyl sulphide.

If, in a preferred embodiment, the enolate salt of the compound II is synthesized by adding strong deprotonating agents (such as, for example, sodium hydride or potassium tertiary butylate), the further addition of acid-binding agents can be dispensed with.

If acid-binding agents are employed, then customary inorganic or organic bases are suitable, sodium hydroxide, sodium carbonate, potassium carbonate and pyridine being mentioned by way of example.

The reaction can be carried out at atmospheric pressure or under elevated pressure, it is preferably effected at atmospheric pressure. The products are worked up by customary methods.

If appropriate, preparation process B can be effected under phase-transfer conditions (W. J. Spillane et al., J. Chem. Soc. Perkin Trans I, (3) 677–9 (1982)). In this event, 0.3 to 1.5 moles of sulphonyl chloride (IV), preferably 0.5 mole, are reacted per mole of starting compound of the formula (II) at 0° to 150° C., preferably at 20° to 70° C. Examples of phase transfer catalysts which can be used are all quaternary ammonium salts, preferably tetraoctylammonium bromide and benzyl-triethylammonium chloride. In this case, all unpolar inert solvents can act as organic solvents, benzene and toluene being preferably employed.

Approximately 1 mole of isocyanate of the formula (V) is reacted per mole of starting compound of the formula II in preparation process $C_\alpha$ at 0° to 100° C., preferably at 20° to 50° C.

Suitable diluents which are optionally added are all inert organic solvents, such as ethers, amides, nitriles, sulphones and sulphoxides.

If appropriate, it is possible to add catalysts to accelerate the reaction. Catalysts which can be very advantageously employed are organotin compounds, such as, for example, dibutyltin dilaurate. The process is preferably effected at atmospheric pressure.

Approximately 1 mole of carbamoyl chloride or thiocarbamoyl chloride of the formula (VI) is reacted per mole of starting compound of the formula (II) in preparation process $C_\beta$ at 0° to 150° C., preferably at 20° to 70° C.

Suitable diluents which are optionally added are all inert polar organic solvents, such as ethers, amides, alcohols, sulphones and sulphoxides.

Diluents which are preferably employed are dimethyl sulphoxide, tetrahydrofuran, dimethylformamide and dimethyl sulphide.

If, in a preferred embodiment, the enolate salt of the compound II is synthesized by adding strong deprotonating agents (such as, for example, sodium hydride or potassium tertiary butylate), the further addition of acid-binding agents can be dispensed with.

If acid-binding agents are employed, then customary inorganic or organic bases are suitable, sodium hydroxide, sodium carbonate, potassium carbonate and pyridine being mentioned by way of example.

The reaction can be carried out at atmospheric pressure or under elevated pressure, preferably under atmospheric pressure. The products are worked up by customary methods.

Approximately 1 mole of chloromonothioformic ester or chlorodithioformic ester of the formula (VII) is reacted per mole of starting compound of the formula (II) in preparation process $D_\alpha$ at 0° to 120° C., preferably at 20° to 60° C.

Suitable diluents which are optionally added are all inert polar organic solvents, such as ethers, amides, alcohols, sulphones and sulphoxides.

Diluents which are preferably employed are dimethyl sulphoxide, tetrahydrofuran, dimethylformamide and dimethyl sulphide.

If, in a preferred embodiment, the enolate salt of the compound II is synthesized by adding strong deprotonating agents (such as, for example, sodium hydride or potassium tertiary butylate), the further addition of acid-binding agents can be dispensed with.

If acid-binding agents are employed, then customary inorganic or organic bases are suitable, sodium hydroxide, sodium carbonate, potassium carbonate and pyridine being mentioned by way of example.

The reaction can be carried out at atmospheric pressure or under elevated pressure, preferably under atmospheric pressure. The products are worked up by customary methods.

The equimolar amount, or an excess, of carbon disulphide is added per mole of starting compound of the formula (II) in preparation process $D_\beta$. This process is preferably effected at temperatures from 0° to 50° C. and, in particular, at 20° to 30° C.

It is often expedient to first prepare the corresponding salt from the compound of the formula (II) by adding a deprotonating agent (such as, for example, potassium tertiary butylate or sodium hydride). The compound (II) is reacted with carbon disulphide until the formation of the intermediate is complete, for example stirring for several hours at room temperature.

The further reaction with the alkyl halide of the formula (VIII) is preferably carried out at 0° to 70° C. and, in particular, at 20° to 50° C. In this process, at least the equimolar amount of alkyl halide is employed.

The process is effected at atmospheric pressure or under elevated pressure, preferably at atmospheric pressure.

Again, the products are worked up by customary methods.

When carrying out process (E) according to the invention, the starting substances of the formula (If) and the appropriate oxidant are employed in approximately equimolar amounts. The products are worked up by the customary methods.

Suitable oxidants for process (E) according to the invention are all reagents which oxidize sulphur, for example halogen such as chlorine and bromine, and their aqueous solutions, or alkali metal such as sodium peroxide and potassium peroxide, salts of oxyhalogen acids such as potassium chlorate, potassium bromate, sodium periodate and sodium perborate, furthermore inorganic persalts such as potassium permanganate, potassium peroxodisulphate and potassium peroxomonosulphate, but also $H_2O_2$ in the presence of transition metal salts such as sodium tungstenate and ammonium molybdate. Organic peroxides such as tert.-butyl hydroperoxide can furthermore be used, but also organic peracids, such as peracetic acid, perpropionic acid and m-chloroperbenzoic acid (MCPBA).

Diluents which can be employed in process (E) according to the invention are all solvents which are inert towards these compounds. The following can preferably be used: hydrocarbons, such as benzine, benzene, toluene, xylene and tetralin, furthermore halogenohydrocarbons such as methylene chloride, chloroform, chlorobenzene and dichlorobenzene, moreover organic acids such as acetic acid and propionic acid, and water.

If process (E) according to the invention is carried out in the presence of a diluent, the reaction temperatures can be varied within a substantial range. In general, the reaction temperatures are between −30° C. and +150° C., preferably between 0° C. and 100° C.

Process (E) according to the invention is generally carried out under atmospheric pressure.

When carrying out process (F) according to the invention, the starting substances of the formula (If) and the appropriate oxidant are employed in approximately twice the equimolar amounts. However, it is also possible to employ the oxidant in a larger excess (up to 2 moles). The products are worked up by the customary methods.

Suitable oxidants for process (F) according to the invention are all reagents which oxidize sulphur, for example halogen such as chlorine and bromine and their aqueous solutions, alkali metal peroxides such as sodium peroxide and potassium peroxide, salts of oxyhalogen acids such as potassium chlorate, potassium bromate, sodium periodate and sodium perborate, furthermore inorganic persalts such as potassium permanganate, potassium peroxodisulphate and potassium peroxomonosulphate, but also $H_2O_2$ in the presence of transition metal salts such as sodium tungstenate and ammonium molybdate. Organic peroxides such as tert.-butyl hydroperoxide can furthermore be used, but also organic peracids such as peracetic acid, perpropionic acid and m-chloroperbenzoic acid (MCPBA).

Diluents which can be employed in process (F) according to the invention are all solvents which are inert towards these compounds. The following can preferably be used: hydrocarbons such as benzine, benzene, toluene, xylene and tetralin, furthermore halogenohydrocarbons such as methylene chloride, chloroform, chlorobenzene and dichlorobenzene, moreover organic acids such as acetic acid and propionic acid, and water.

If process (F) according to the invention is carried out in the presence of a diluent, the reaction temperatures can be varied within a substantial range. In general, the reaction temperatures are between −30° C. and +150° C., preferably between 0° C. and 100° C.

Process (F) according to the invention is generally carried out under atmospheric pressure.

EXAMPLE 1

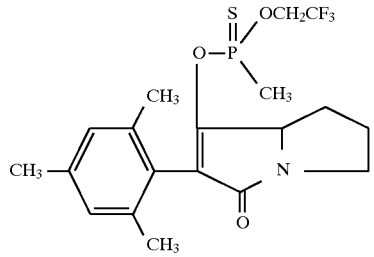

11.1 g of 3-(2,4,6-trimethyl-phenyl)-1,5-trimethylene-2,4-pyrrolidine-dione (0.04 mol), 7 g (0.05 mol) of potassium carbonate and 0.5 g of (DABCO) (1,4-diazabicyclo[2.2.2]octane) (4.5 mmol) are suspended in 100 ml of acetonitrile, 9.5 g (0.05 mol) of 2,2,2-trifluoroethyl methanethiochlorophosphonate are added at 20° C., and the mixture is stirred for one day at 20° C. The solid is subsequently filtered off with suction, and the solution is evaporated on a rotary evaporator. The residue is filtered over silica gel (eluent: hexane:ethyl acetate=8:2).

8.9 g (52% of theory) of 4-(2,2,2-trifluoroethoxy-methanethiophosphoryl)-3-(2,4,6-trimethylphenyl)-1,5-trimethylene-3-pyrrolin-2-one are obtained, of melting point 109° C.

The following are obtained analogously:

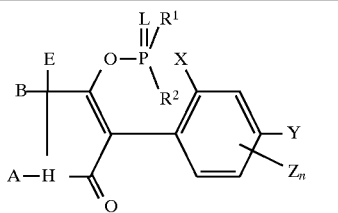

| Example No. | X | Y | Zn | L | R¹ | R² | A | B | E | Physical data |
|---|---|---|---|---|---|---|---|---|---|---|
| 2 | $CH_3$ | $CH_3$ | 6-$CH_3$ | S | $OC_2H_5$ | $nC_3H_7S$ | $-(CH_2)_3-$ | | H | $n_D^{20}$ 1.5662 |
| 3 | $CH_3$ | $CH_3$ | 6-$CH_3$ | O | $N(CH_3)_2$ | $N(CH_3)_2$ | $-(CH_2)_3-$ | | H | $n_D^{20}$ 1.5382 |
| 4 | $CH_3$ | $CH_3$ | 6-$CH_3$ | S | $CH_3$ | $SCH_2-C(CH_3)_3$ | $-(CH_2)_3-$ | | H | $n_D^{20}$ 1.5636 |
| 5 | $CH_3$ | $CH_3$ | 6-$CH_3$ | S | $CH_3$ | $OCH_3$ | $-(CH_2)_3-$ | | H | $n_D^{20}$ 1.5344 |
| 6 | $CH_3$ | $CH_3$ | 6-$CH_3$ | S | $CH_3$ | $OC_2H_5$ | $-(CH_2)_3-$ | | H | $n_D^{20}$ 1.5507 |
| 7 | $CH_3$ | $CH_3$ | 6-$CH_3$ | S | $CH_3$ | $OC_3H_7$-i | $-(CH_2)_3-$ | | H | Fp: 32° C. |
| 8 | $CH_3$ | $CH_3$ | 6-$CH_3$ | S | $CH_3$ | $OC_4H_9$-sec | $-(CH_2)_3-$ | | H | Fp: 89° C. |
| 9 | $CH_3$ | $CH_3$ | 6-$CH_3$ | S | $CH_3$ | $OC_4H_9$-iso | $-(CH_2)_3-$ | | H | |
| 10 | $CH_3$ | $CH_3$ | 6-$CH_3$ | S | $C_2H_5$ | $OCH_3$ | $-(CH_2)_3-$ | | H | Fp: 40° C. |
| 11 | $CH_3$ | $CH_3$ | 6-$CH_3$ | S | $C_2H_5$ | $OC_3H_7$-i | $-(CH_2)_3-$ | | H | |
| 12 | $CH_3$ | $CH_3$ | 6-$CH_3$ | S | $C_2H_5$ | $OC_4H_9$-sec | $-(CH_2)_3-$ | | H | |
| 13 | $CH_3$ | $CH_3$ | 6-$CH_3$ | S | $C_2H_5$ | $OC_4H_9$-i | $-(CH_2)_3-$ | | H | |
| 14 | $CH_3$ | $CH_3$ | 6-$CH_3$ | S | $C_2H_5$ | $SCH_3$ | $-(CH_2)_4-$ | | H | $n_D^{20}$ 1.5662 |
| 15 | $CH_3$ | $CH_3$ | 6-$CH_3$ | S | $C_2H_5$ | $SC_2H_5$ | $-(CH_2)_4-$ | | H | |
| 16 | $CH_3$ | $CH_3$ | 6-$CH_3$ | S | $C_2H_5$ | $SC_3H_7$-i | $-(CH_2)_4-$ | | H | |
| 17 | $CH_3$ | $CH_3$ | 6-$CH_3$ | S | $C_2H_5$ | $SCH_2CH=CH_2$ | $-(CH_2)_4-$ | | H | |
| 18 | $CH_3$ | $CH_3$ | 6-$CH_3$ | S | $C_2H_5$ | $SCH_2C≡CH$ | $-(CH_2)_4-$ | | H | |
| 19 | $CH_3$ | $CH_3$ | 6-$CH_3$ | S | $C_2H_5$ | $SC_4H_9$-sec. | $-(CH_2)_4-$ | | H | |
| 20 | $CH_3$ | $CH_3$ | 6-$CH_3$ | S | $C_2H_5$ | $SC_4H_9$-iso | $-(CH_2)_4-$ | | H | |
| 21 | $CH_3$ | $CH_3$ | 6-$CH_3$ | S | $C_2H_5$ | S-cyclohexyl | $-(CH_2)_4-$ | | H | |
| 22 | $CH_3$ | $CH_3$ | 6-$CH_3$ | S | $CH_3$ | $SC_3H_7$-n | $-(CH_2)_4-$ | | H | |
| 23 | $CH_3$ | $CH_3$ | 6-$CH_3$ | S | $OC_2H_5$ | $OC_2H_5$ | $-(CH_2)_4-$ | | H | m.p.: 35° C. |
| 24 | $CH_3$ | $CH_3$ | 6-$CH_3$ | S | O-phenyl | $OC_2H_5$ | $-(CH_2)_4-$ | | H | |
| 25 | $CH_3$ | $CH_3$ | 6-$CH_3$ | S | $CH_3$ | $OC_3H_7$-i | $C_3H_7$-i | H | H | |
| 26 | $CH_3$ | $CH_3$ | 6-$CH_3$ | S | $CH_3$ | $OC_3H_7$-i | cyclohexyl | H | H | |
| 27 | $CH_3$ | $CH_3$ | 6-$CH_3$ | S | $C_2H_5$ | O-(2-F-phenyl) | $-(CH_2)_4-$ | | H | |
| 28 | $CH_3$ | $CH_3$ | 6-$CH_3$ | S | $OC_2H_5$ | O-(4-$SCH_3$-phenyl) | $-(CH_2)_4-$ | | H | |
| 29 | $CH_3$ | $CH_3$ | 6-$CH_3$ | S | n-$C_4H_9$ | O-(3-F-phenyl) | $-(CH_2)_4-$ | | H | |

-continued (Ia)

| Example No. | X | Y | Zn | L | R¹ | R² | A | B | E | Physical data |
|---|---|---|---|---|---|---|---|---|---|---|
| 30 | $CH_3$ | $CH_3$ | 6-$CH_3$ | S | $CH_3$ | $OC_2H_5$ | —$(CH_2)_4$— | | H | m.p. 42° C. |
| 31 | $CH_3$ | $CH_3$ | 6-$CH_3$ | S | $C_2H_5$ | $OCH_3$ | —$(CH_2)_4$— | | H | $n_D^{20}$ 1.5757 |
| 32 | $CH_3$ | $CH_3$ | 6-$CH_3$ | S | $C_2H_5$ | $OC_2H_5$ | —$(CH_2)_4$— | | H | m.p. 75° C. |
| 33 | $CH_3$ | $CH_3$ | 6-$CH_3$ | S | $CH_3$ | $OC_3H_7$-i | —$(CH_2)_4$— | | H | m.p. 32° C. |
| 34 | $CH_3$ | $CH_3$ | 6-$CH_3$ | S | $C_2H_5$ | $OCH_3$ | (cyclopentyl) | | H | $n_D^{20}$ 1.5515 |
| 35 | $CH_3$ | $CH_3$ | 6-$CH_3$ | S | $OC_2H_5$ | $OC_2H_5$ | $C_3H_7$-i | $CH_3$ | H | $n_D^{20}$ 1.5076 |
| 36 | $CH_3$ | $CH_3$ | 6-$CH_3$ | S | $CH_3$ | $OC_2H_5$ | (cyclopentyl) | | H | $n_D^{20}$ 1.5505 |
| 37 | $CH_3$ | $CH_3$ | 6-$CH_3$ | S | $CH_3$ | $OC_3H_7$-i | (cyclopentyl) | | H | $n_D^{20}$ 1.5452 |
| 38 | $CH_3$ | $CH_3$ | 6-$CH_3$ | S | $CH_3$ | $OC_2H_5$ | $C_3H_7$-i | $CH_3$ | H | $n_D^{20}$ 1.5194 |
| 39 | $CH_3$ | $CH_3$ | 6-$CH_3$ | S | $C_2H_5$ | $OCH_3$ | $C_3H_7$-i | $CH_3$ | H | $n_D^{20}$ 1.5328 |
| 40 | $CH_3$ | $CH_3$ | 6-$CH_3$ | S | $C_2H_5$ | $OC_2H_5$ | $C_3H_7$-i | $CH_3$ | H | $n_D^{20}$ 1.5237 |
| 41 | $CH_3$ | $CH_3$ | 6-$CH_3$ | S | $OC_2H_5$ | $OC_2H_5$ | —$(CH_2)_3$— | | H | m.p. 42° C. |
| 42 | $CH_3$ | $CH_3$ | 6-$CH_3$ | O | $OC_2H_5$ | $SC_3H_7$-i | —$(CH_2)_3$— | | H | $n_D^{20}$ 1.5392 |
| 43 | $CH_3$ | $CH_3$ | 6-$CH_3$ | S | $OCH_3$ | $N(CH_3)_2$ | —$(CH_2)_3$— | | H | |
| 44 | $CH_3$ | $CH_3$ | 6-$CH_3$ | S | $CH_3$ | $SCH(CH_3)C_2H_5$ | —$(CH_2)_3$— | | H | $n_D^{20}$ 1.5412 |
| 45 | $CH_3$ | $CH_3$ | 6-$CH_3$ | O | $C_2H_5O$ | $SCH(CH_3)C_2H_5$ | —$(CH_2)_3$— | | H | $n_D^{20}$ 1.5405 |
| 46 | $CH_3$ | $CH_3$ | 6-$CH_3$ | O | $C_2H_5O$ | $SC_3H_7$-i | —$(CH_2)_3$— | | H | |
| 47 | $CH_3$ | $CH_3$ | 6-$CH_3$ | O | $CH_3O$ | $SC_3H_7$-i | —$(CH_2)_3$— | | H | |
| 48 | $CH_3$ | $CH_3$ | 6-$CH_3$ | O | n-$C_4H_9O$ | $SC_3H_7$-i | —$(CH_2)_3$— | | H | |
| 49 | $CH_3$ | $CH_3$ | 6-$CH_3$ | O | $CH_3O$ | $SC_4H_9$-sek | —$(CH_2)_3$— | | H | |
| 50 | $CH_3$ | $CH_3$ | 6-$CH_3$ | O | n-$C_4H_9$ | $SC_4H_9$-sek | —$(CH_2)_3$— | | H | |

EXAMPLE 51

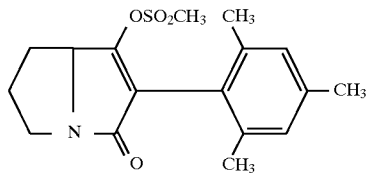

2.58 g (0.01 mol) of 3-(2,4,6-trimethyl-phenyl)-1,5-trimethylene-2,4-pyrrolidine-dione are suspended in 20 ml of absolute dimethylformamide at room temperature. To this suspension there is added, in portions, 0.3 g of an 80% suspension of sodium hydride in paraffin oil. Stirring is continued until evolution of hydrogen has ceased. The mixture is then cooled to 10° C., and 1.6 g (0.014 mol) of methanesulphonyl chloride are added. Stirring is continued for 1 hour at room temperature, and the mixture is then stirred in 100 ml of distilled water, the mixture is extracted (3 times) using methylene chloride, the organic phase is washed once using 40 ml of 5% strength hydrochloric acid and dried over sodium sulphate, and the solvent is then stripped off in a rotary evaporator.

The crude product is chromatographed for purification (eluent mixture: ethyl acetate/cyclohexane 1:1)
Yield: 2.51 g (75%) of the title compound.

EXAMPLE 52

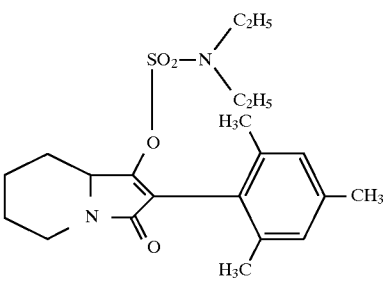

2.71 g (0.01 mol) of 3-(2,4,6-trimethyl-phenyl)-1,5-tetramethylene-2,4-pyrrolidine-dione are suspended in 15 ml of toluene. 62 mg (0.2 mmol) of tetra-butylammonium bromide, 0.86 g (0.005 mol) of diethylsulphamoyl chloride and 15 ml of 30% by weight strength sodium hydroxide solution are added in succession.

The vigorously stirred mixture is brought to 50° C. The reaction is allowed to proceed for 1.5 hours at this temperature. Then, 100 ml of methylene chloride and 100 ml of water are added, the organic phases are separated, and the aqueous phase is re-extracted twice with methylene chloride. The combined organic phases are washed with water and dried over $Na_2SO_4$.

The mixture is chromatographed for purification (eluent: ethyl acetate/cyclohexane 1:3)

Yield: 400 mg (10%) of colourless, viscous oil

The following are obtained analogously:

| Example No. | X | Y | Zn | $R^3$ | A | B | E | Physical data |
|---|---|---|---|---|---|---|---|---|
| 53 | $CH_3$ | $CH_3$ | 6-$CH_3$ | $CH_3$ | $-(CH_2)_3-$ | | H | |
| 54 | $CH_3$ | $CH_3$ | 6-$CH_3$ | $CH_3$ | $-(CH_2)_4-$ | | H | m.p. 115–118° C. |
| 55 | $CH_3$ | $CH_3$ | 6-$CH_3$ | $CH_2$-phenyl | $-(CH_2)_4-$ | | H | m.p. 163–165° C. |
| 56 | $CH_3$ | $CH_3$ | 6-$CH_3$ | $CH_2$-phenyl | $-(CH_2)_3-$ | | H | m.p. 116–118° C. |
| 57 | $CH_3$ | $CH_3$ | 6-$CH_3$ | phenyl | $-(CH_2)_3-$ | | H | |
| 58 | $CH_3$ | $CH_3$ | 6-$CH_3$ | 4-Cl-phenyl | $-(CH_2)_3-$ | | H | m.p. 123–126° C. |
| 59 | $CH_3$ | $CH_3$ | 6-$CH_3$ | $CHCl_2$ | $-(CH_2)_3-$ | | H | |
| 60 | $CH_3$ | $CH_3$ | 6-$CH_3$ | $CH_2$-(3,4-Cl$_2$-phenyl) | $-(CH_2)_3-$ | | H | |
| 61 | $CH_3$ | $CH_3$ | 6-$CH_3$ | $CH_2$-(4-Cl-phenyl) | $-(CH_2)_4-$ | | H | m.p. 151–154° C. |
| 62 | $CH_3$ | $CH_3$ | 6-$CH_3$ | 3,4-Cl$_2$-phenyl | $-(CH_2)_4-$ | | H | |
| 63 | $CH_3$ | $CH_3$ | 6-$CH_3$ | n-$C_4H_9$ | $-(CH_2)_4-$ | | H | |
| 64 | Cl | $CH_3$ | 6-Cl | $CH_3$ | $-(CH_2)_3-$ | | H | |
| 65 | $CH_3$ | $CH_3$ | 5-$CH_3$ | $CH_3$ | $-(CH_2)_3-$ | | H | |
| 66 | Cl | H | 6-Cl | n-$C_4H_9$ | $-(CH_2)_3-$ | | H | |
| 67 | $CH_3$ | $CH_3$ | 5-$CH_3$ | n-$C_4H_9$ | $-(CH_2)_3-$ | | H | |
| 68 | $CH_3$ | $CH_3$ | 6-$CH_3$ | n-$C_{12}H_{25}$ | $-(CH_2)_3-$ | | H | m.p. 65° C. |
| 69 | $CH_3$ | $CH_3$ | 6-$CH_3$ | n-$C_{12}H_{25}$ | $-(CH_2)_4-$ | | H | m.p. 85–87° C. |
| 70 | $CH_3$ | $CH_3$ | 6-$CH_3$ | pentachloro-bicyclic | $-(CH_2)_4-$ | | H | |

-continued

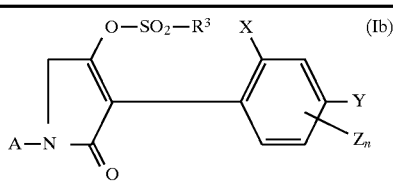

(Ib)

| Example No. | X | Y | Zn | R³ | A | B | E | Physical data |
|---|---|---|---|---|---|---|---|---|
| 71 | $CH_3$ | $CH_3$ | 6-$CH_3$ | $CH(CH_3)_2$ | $-(CH_2)_4-$ | | H | |
| 72 | $CH_3$ | $CH_3$ | 6-$CH_3$ | $CH_3$ | cyclopentyl | H | H | |
| 73 | $CH_3$ | $CH_3$ | 6-$CH_3$ | $CH_3$ | $CH(CH_3)_2$ | H | H | |
| 74 | $CH_3$ | $CH_3$ | 6-$CH_3$ | n-$C_4H_9$ | cyclopentyl | H | H | |
| 75 | $CH_3$ | $CH_3$ | 6-$CH_3$ | n-$C_4H_9$ | $CH(CH_3)_2$ | H | H | |
| 76 | $CH_3$ | $CH_3$ | 6-$CH_3$ | $CH(CH_3)_2$ | $-(CH_2)_3-$ | | H | |
| 77 | $CH_3$ | $CH_3$ | 6-$CH_3$ | $-N(C_2H_5)_2$ | $-(CH_2)_3-$ | | H | |
| 78 | $CH_3$ | $CH_3$ | 6-$CH_3$ | $-N(CH_3)_2$ | $-(CH_2)_4-$ | | H | |

EXAMPLE 79

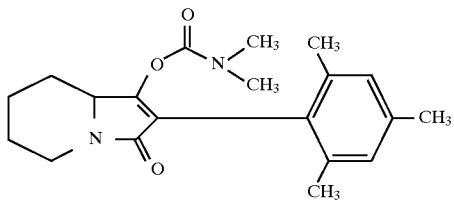

2.71 g (0.001 mol) of 3-(2,4,6-trimethyl-phenyl)-1,5-tetramethylene-2,4-pyrrolidine-dione are suspended in 15 ml of absolute dimethylformamide, at room temperature. To this suspension there is added, in portions, 0.3 g (0.01 mol) of an 80% suspension of sodium hydride in paraffin oil. Stirring is continued until the evolution of hydrogen has ceased. The mixture is then cooled to 10° C., and 1.23 g (0.013 mol) of dimethylcarbamoyl chloride are added. The mixture is allowed to come to room temperature, warmed to 80° C., and stirred at this temperature for 1 hour. For working up, the mixture is stirred into 35 ml of a 1% strength NaOH solution, and the mixture is extracted 3 times using methyl chloride. The organic phase is washed in succession with 15 ml of water and 15 ml of 5% strength hydrochloric acid and then dried over sodium sulphate. After the drying agent has been removed and the solvent has been stripped in a rotary evaporator, the product is purified by chromatography. (Eluent: ethyl acetate/cyclohexane 1:5)
Yield: 3.2 g (94%) of the title compound
The following are obtained analogously:

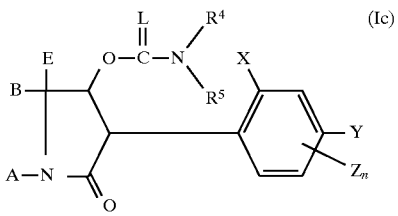

(Ic)

| Exaple No. | X | Y | Zn | L | R⁴ | R⁵ | A | B | E | Physical data |
|---|---|---|---|---|---|---|---|---|---|---|
| 80 | $CH_3$ | $CH_3$ | 6-$CH_3$ | S | $CH_3$ | $CH_3$ | $-(CH_2)_4-$ | | H | m.p. 188–189° C. |
| 81 | Cl | H | 6-Cl | O | $CH_3$ | $CH_3$ | $-(CH_2)_4-$ | | H | m.p. 119–121° C. |
| 82 | Cl | H | 6-Cl | S | $CH_3$ | $CH_3$ | $-(CH_2)_4-$ | | H | m.p. 158–161° C. |
| 83 | $CH_3$ | $CH_3$ | 6-$CH_3$ | O | $CH_3$ | $CH_3$ | $-(CH_2)_3-$ | | H | |
| 84 | $CH_3$ | $CH_3$ | 6-$CH_3$ | S | $CH_3$ | $CH_3$ | $-(CH_2)_3-$ | | | |
| 85 | $CH_3$ | $CH_3$ | 6-$CH_3$ | O | $-CH_2-CH=CH_2$ | $-CH_2-CH=CH_2$ | $-(CH_2)_3-$ | | H | |
| 86 | $CH_3$ | $CH_3$ | 6-$CH_3$ | O | $CH_3$ | phenyl | $-(CH_2)_3-$ | | H | |
| 87 | $CH_3$ | $CH_3$ | 6-$CH_3$ | O | $C_3H_7(n)$ | $C_3H_7(n)$ | $-(CH_2)_3-$ | | H | |
| 88 | $CH_3$ | $CH_3$ | 6-$CH_3$ | O | $-(CH_2)_5-$ | | $-(CH_2)_3-$ | | H | |
| 89 | $CH_3$ | $CH_3$ | 6-$CH_3$ | S | $-(CH_2)_2-O-(CH_2)_2-$ | | $-(CH_2)_3-$ | | H | |
| 90 | $CH_3$ | $CH_3$ | 6-$CH_3$ | S | $-(CH_2)_5-$ | | $-(CH_2)_3-$ | | H | m.p. 112–116° C. |
| 91 | $CH_3$ | $CH_3$ | 6-$CH_3$ | S | $C_2H_5$ | $C_2H_5$ | $-(CH_2)_3-$ | | H | m.p. 112–116° C. |
| 92 | $CH_3$ | $CH_3$ | 6-$CH_3$ | S | $C_2H_5$ | phenyl | $-(CH_2)_3-$ | | H | m.p. 106–110° C. |
| 93 | $CH_3$ | $CH_3$ | 6-$CH_3$ | S | $-(CH_2)_2-CH(CH_3)-(CH_2)_2-$ | | $-(CH_2)_3-$ | | H | |

EXAMPLE 94

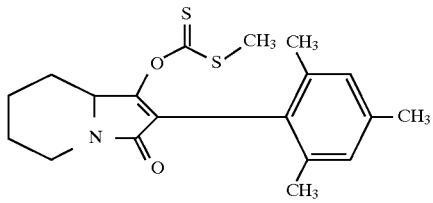

EXAMPLE 95

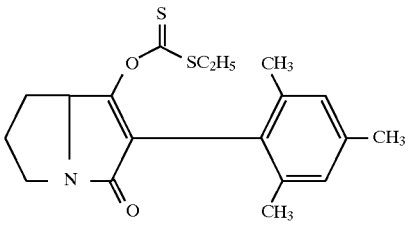

2.71 g (0.01 mol) of 3-(2,4,6-trimethyl-phenyl)-1,5-tetramethylene-2,4-pyrrolidine-dione are suspended in 20 ml of absolute dimethylformamide, at room temperature. To this suspension there is added, in portions, 0.3 g of an 80% suspension of sodium hydride in paraffin oil. Stirring is continued until the evolution of hydrogen has ceased.

3 ml of carbon disulphide are then added, and the mixture is stirred for three hours at room temperature. Three ml of methyl iodide are added, and stirring is subsequently continued for 3 hours at room temperature.

For working-up, a mixture of 100 ml of water and 100 ml of methylene chloride is poured into the reaction mixture, and the aqueous phase is separated off and re-extracted twice using methylene chloride. The combined organic phases are dried over sodium sulphate. After the drying agent has been separated off and the solvent-has been fastened, the product is chromatographed. (Eluent: ethyl acetate/cyclohexane 4:1)

Yield: 1.5 g (41.5%) of the title compound 2.58 g (0.01 mol) of 3-(2,4,6-trimethyl-phenyl)-1,5-trimethylene-2,4-pyrrolidine-dione are suspended in 20 ml of absolute dimethylformamide, at room temperature. To this suspension there is added, in portions, 0.3 g of an 80% suspension of sodium hydride in paraffin oil. Stirring is continued until the evolution of hydrogen has ceased.

1.5 ml (0.014 mol) of S-ethyl chlorothioformate are then slowly added dropwise. When the addition has ended, stirring is continued for 1 hour at room temperature, and then 100 ml of water are added, the mixture is extracted 3 times using methylene chloride, and the organic phase is washed once using 40 ml of 5% strength hydrochloric acid, dried and concentrated.

Yield: 1.34 g (38.8%)

The following are obtained analogously:

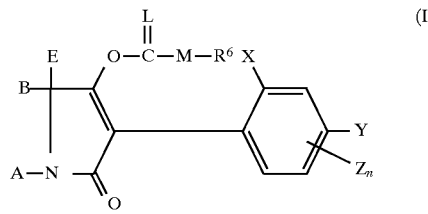

(Id)

| Example No. | X | Y | Zn | L | M | R⁶ | A | B | E | Physical Data |
|---|---|---|---|---|---|---|---|---|---|---|
| 96 | $CH_3$ | $CH_3$ | 6-$CH_3$ | S | O | $C_2H_5$ | | $-(CH_2)_3-$ | H | |
| 97 | $CH_3$ | $CH_3$ | 6-$CH_3$ | O | S | $C_2H_5$ | | $-(CH_2)_3-$ | H | oil |
| 98 | $CH_3$ | $CH_3$ | 6-$CH_3$ | O | S | $C_2H_5$ | | $-(CH_2)_4-$ | H | oil |
| 99 | $CH_3$ | $CH_3$ | 6-$CH_3$ | S | S | $C_2H_5$ | | $-(CH_2)_4-$ | H | |
| 100 | $CH_3$ | $CH_3$ | 6-$CH_3$ | S | S | i-$C_3H_7$ | | $-(CH_2)_4-$ | H | |
| 101 | $CH_3$ | $CH_3$ | 6-$CH_3$ | S | S | n-$C_4H_9$ | | $-(CH_2)_4-$ | H | |
| 102 | $CH_3$ | $CH_3$ | 6-$CH_3$ | S | S | $-CH_2$-C₆H₅ | | $-(CH_2)_4-$ | H | m.p. 140° C. |
| 103 | $CH_3$ | $CH_3$ | 6-$CH_3$ | S | S | $-CH_2-CH=CH_2$ | | $-(CH_2)_4-$ | H | |
| 104 | $CH_3$ | $CH_3$ | 6-$CH_3$ | S | S | $-CH_2-C\equiv CH$ | | $-(CH_2)_4-$ | H | m.p. 92–94° C. |
| 105 | $CH_3$ | $CH_3$ | 6-$CH_3$ | S | S | $-CH_2-CH=CH_2$ | | $-(CH_2)_3-$ | H | m.p. 103–105° C. |
| 106 | $CH_3$ | $CH_3$ | 6-$CH_3$ | S | S | $C_2H_5$ | | $-(CH_2)_3-$ | H | |
| 107 | $CH_3$ | $CH_3$ | 6-$CH_3$ | S | S | $CH_3$ | | cyclopentyl | H | m.p. 141–142° C. |
| 108 | $CH_3$ | $CH_3$ | 6-$CH_3$ | O | S | n-$C_4H_9-$ | | $-(CH_2)_3-$ | H | oil |
| 109 | $CH_3$ | $CH_3$ | 6-$CH_3$ | O | S | $(CH_3)_2CH-CH_2-CHCH_3-$ | | $-(CH_2)_3-$ | H | oil |
| 110 | $CH_3$ | $CH_3$ | 6-$CH_3$ | O | S | $-CH_2$-C₆H₅ | | $-(CH_2)_4-$ | H | oil |
| 111 | $CH_3$ | $CH_3$ | 6-$CH_3$ | O | S | n-$C_4H_9-$ | | $-(CH_2)_4-$ | H | oil |
| 112 | $CH_3$ | $CH_3$ | 6-$CH_3$ | O | S | t-$C_4H_9-$ | | $-(CH_2)_4-$ | H | ¹H-NMR (200 MHz, CDCl₃) δ = 1.37 (s,9H) 4.28 (dd,1H) 4.4 (dd,1H) 6.85 (s,2H) |
| 113 | $CH_3$ | $CH_3$ | 6-$CH_3$ | O | S | i-$C_3H_7-$ | | $-(CH_2)_4-$ | H | oil |
| 114 | $CH_3$ | $CH_3$ | 6-$CH_3$ | O | S | $(CH_3)_2CH-CH_2-CHCH_3-$ | | $-(CH_2)_4-$ | H | oil |
| 115 | $CH_3$ | $CH_3$ | 6-$CH_3$ | O | S | $(CH_3)_3C-(CH_2)_2-$ | | $-(CH_2)_4-$ | H | oil |
| 116 | $CH_3$ | $CH_3$ | 6-$CH_3$ | O | S | $(CH_3)_3C-(CH_2)-$ | | $-(CH_2)_4-$ | H | m.p. 119° C. |
| 117 | $CH_3$ | $CH_3$ | 6-$CH_3$ | O | S | s-$C_4H_9-$ | | $-(CH_2)_4-$ | H | oil |
| 118 | $CH_3$ | $CH_3$ | 6-$CH_3$ | O | S | i-$C_5H_{11}-$ | | $-(CH_2)_4-$ | H | oil |
| 119 | $CH_3$ | $CH_3$ | 6-$CH_3$ | O | S | n-$C_4H_9-$ | | $-(CH_2)_3-S-$ | H | oil |
| 120 | $CH_3$ | $CH_3$ | 6-$CH_3$ | O | S | $-CH_2$-C₆H₅ | | $-(CH_2)_2-S-CH_2-$ | H | oil |
| 121 | $CH_3$ | $CH_3$ | 6-$CH_3$ | O | S | $(CH_3)_3-CH_2-$ | | $-(CH_2)_2-S-CH_2-$ | H | oil |
| 122 | $CH_3$ | $CH_3$ | 6-$CH_3$ | O | S | t-$C_4H_9-$ | | $-(CH_2)_2-S-CH_2-$ | H | oil |
| 123 | $CH_3$ | $CH_3$ | 6-$CH_3$ | O | S | i-$C_3H_7-$ | | $-(CH_2)_2-S-CH_2-$ | H | oil |
| 124 | $CH_3$ | $CH_3$ | 6-$CH_3$ | O | S | $(CH_3)_2CH-CH_2-CHCH_3-$ | | $-(CH_2)_2-S-CH_2-$ | H | m.p. 135–136° C. |
| 125 | $CH_3$ | $CH_3$ | 6-$CH_3$ | O | S | $(CH_3)_3C-(CH_2)_2-$ | | $-(CH_2)_2-S-CH_2-$ | H | oil |
| 126 | $CH_3$ | $CH_3$ | 6-$CH_3$ | O | S | s-$C_4H_9-$ | | $-(CH_2)_2-S-CH_2-$ | H | oil |
| 127 | $CH_3$ | $CH_3$ | 6-$CH_3$ | O | S | n-$C_4H_9-$ | | cyclopentyl | H | oil |
| 128 | $CH_3$ | $CH_3$ | 6-$CH_3$ | O | S | n-$C_4H_9-$ | i-$C_3H_7-$ | H | H | oil |

-continued

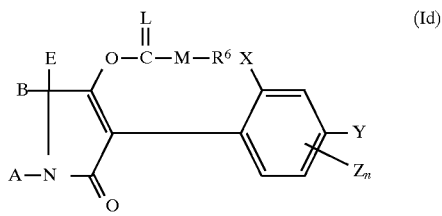
(Id)

| Example No. | X | Y | Zn | L | M | R⁶ | A | B | E | Physical Data |
|---|---|---|---|---|---|---|---|---|---|---|
| 129 | $CH_3$ | $CH_3$ | 6-$CH_3$ | O | S | t-$C_4H_9$— | cyclopentyl | H | H | m.p. 169–170° C. |
| 130 | $CH_3$ | $CH_3$ | 6-$CH_3$ | O | S | i-$C_3H_7$— | cyclopentyl | H | H | m.p. 115–116° C. |
| 131 | $CH_3$ | $CH_3$ | 6-$CH_3$ | O | S | $(CH_3)_2CH-CH_2-CHCH_3-$ | cyclopentyl | H | H | oil |
| 132 | $CH_3$ | $CH_3$ | 6-$CH_3$ | O | S | t-$C_4H_9$— | i-$C_3H_7$— | H | H | m.p. 160° C. |
| 133 | $CH_3$ | $CH_3$ | 6-$CH_3$ | O | S | i-$C_3H_7$— | i-$C_3H_7$— | H | H | m.p. 115° C. |
| 134 | $CH_3$ | $CH_3$ | 6-$CH_3$ | O | S | $(CH_3)_2CH-CH_2-CHCH_3-$ | i-$C_3H_7$— | H | H | m.p. 70° C. |
| 135 | $CH_3$ | $CH_3$ | 6-$CH_3$ | O | S | $(CH_3)_3C-(CH_2)_2-$ | i-$C_3H_7$— | H | H | m.p. 83–84° C. |
| 136 | $CH_3$ | $CH_3$ | 6-$CH_3$ | O | S | $(CH_3)_3C-CH_2-$ | i-$C_3H_7$— | H | H | m.p. 103° C. |

The active compounds are suitable for combating animal pests, in particular those of the class of the Arachuida and of the order of mites (Acarina) which are encountered in agriculture, in forestry, in the protection of stored products and of materials, and in the hygiene field, and they have good plant tolerance and favourable toxicity to warm-blooded animals. They are active against normally sensitive and resistant species and against all or some stages of development. The abovementioned pests include:

From the order of the Acarina, for example *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp.*

The active compounds according to the invention are not only active against plant pests, hygiene pests and pests of stored products, but also, in the veterinary medicine sector, against animal parasites (ectoparasites) such as scaly ticks, argasidae, scab mites and trombidae.

They are active against normally sensitive and resistant species and strains and against all parasitic and non-parasitic stages of development of the ecto-parasites.

The active compounds according to the invention are distinguished by a powerful acaricidal activity. They can be employed with particularly good success against mites which damage plants, such as, for example, against the common spider mite (*Tetranychus urticae*).

The active compounds according to the invention can furthermore be used as defoliants, desiccants, agents for destroying broad-leaved plants and, in particular, as weed-killers. By weeds, in the broadest sense, there are to be understood all plants which grow in locations-where they are undesired. Whether the substances according to the invention act as total or selective herbicides depends essentially on the amount used.

It is characteristic of the compounds according to the invention that they have a selective activity against monocotyledon weeds when used in the pre- or post-emergence method, while being well tolerated by crop plants.

The active compounds according to the invention can be used, for example, in connection with the following plants:

Monocotyleonous weeds of the genera: Eschinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous cultures of the genera: Oryza, Zea, Triticum, Hordeum, Avena, Secale, Sorghum, Panicum, Saccharum, Ananas, Asparagus and Allium.

Dicotyledonous cultures of the genera: Gossypium, Glycine, Beta, Daucus, Phaseolus, Pisum, Solanum, Linum,. Ipomoea, Vicia, Nicotiana, Lycopersicon, Arachis, Brassica, Lactuca, Cucumis, Cucurbita.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings-and hopfields, and for the selective combating of weeds in annual cultures.

In this context, the active compounds according to the invention not only have an excellent action against harmful plants, but they are also well tolerated by important crop plants, such as, for example, wheat, cotton, soya beans, citrus fruit and sugar beet, and they can therefore be employed as selective weed killers.

The active compounds can be converted into the customary formulations, such as solutions, emulsions, suspensions, powders, foams, pastes, granules, aerosols, natural and synthetic materials impregnated with active compound, fine capsules in polymeric substances and in coating compositions for seed, furthermore in formulations used with burning equipment, such as fumigating cartridges, fumigating cans, fumigating coils and the like, and also ULV cold-mist and warm-mist formulations.

These formulations are produced in a known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers there are meant liquids which are gaseous at ambient temperature and under atmospheric pressure, such as aerosol propellant, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilants, acaricides, nematicides, herbicides or fungicides. The insecticides include for example, inter alia, phosphoric esters, carbamates, carboxylic esters, chlorinated hydrocarbons, phenylureas, and substances produced by microorganisms.

The active compounds according to the invention can furthermore be present in their commercially available formulations and in the use forms prepared from these formulations as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are applied in a customary manner appropriate for the use forms.

The active compounds which can be used according to the invention are also suitable for combating mites, ticks etc. in the field of animal keeping and livestock husbandry, it being possible to achieve better results, for example higher milk yields, higher weight, more beautiful animal pelt, longer life, inter alia, by combating the pests.

The active compounds which can be used according to the invention are administered in this field in a known maner, such as by oral administration, in the form of, for example, tablets, capsules, drenches, granules, by dermal or external administration, for example in the form of dipping, spraying, pouring-on and spotting-on, and powdering, as well as by parenteral administration, for example in form of injection, as well as, furthermore, by the "feed-through" method. Besides, administration in the form of shaped articles (collar, ear tag) is also possible.

EXAMPLE A

Phaedon Larvae Test

Solvent: 7 parts by weight of dimethylformamide/P compound: acetone

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), while the leaves are still moist.

After the specified period of time, the destruction in % is determined. 100% means that all the beetle larvae have been killed; 0% means that none of the beetle larvae have been killed.

In this test, a superior activity compared with the prior art is shown, for example, by the following compounds of the preparation examples: (1), (2), (4), (59).

TABLE A

Phaedon larvae test

| Active Compound | Active Compound Concentration in % | Mortality in % after 2 days |
|---|---|---|
| Known from U.S. Pat. No. 4,985,063, Ex. No. 249 (structure with O-C(=O)-O-C(CH₃)₃) | 0.1 | 0 |
| according to the invention, Ex. No. 112 (structure with S-C(=O)-O-C(CH₃)₃) | 0.1 | 50 |

TABLE B

Plutella test

| Active Compound | Active Compound Concentration in % | Mortality in % after 2 days |
|---|---|---|
| Known from U.S. Pat. No. 4,985,063, Ex. No. 249 (structure with O-C(=O)-O-C(CH₃)₃) | 0.1 | 0 |
| according to the invention, Ex. No. 112 (structure with S-C(=O)-O-C(CH₃)₃) | 0.1 | 67 |

EXAMPLE B

Plutella Test

Solvent: 7 parts by weight of dimethylformamide/P compound: acetone

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified period of time, the destruction in % is determined. 100% means that all the caterpillars have been killed; 0% means that none of the beetle larvae have been killed.

In this test, a superior activity compared with the prior art is, shown, for example, by the following compounds of the preparation examples: (2).

EXAMPLE C

Nephotettix Test

Solvent: 7 parts by weight of dimethylformamide/P compound: acetone

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with larvae of the green leafhopper (*Nephotettix cincticeps*) while the seedlings are still moist.

After the specified period of time, the destruction in % is determined. 100% means that all cicadas have been killed; 0% means that none of the cicadas have been killed.

In this test, a superior activity compared with the prior art is shown, for example, by the following compounds of the preparation examples: (1), (4), (53), (59).

TABLE C

Nepholettix test

| Active Compound | Active Compound Concentration in % | Mortality in % after 6 days |
|---|---|---|
| Known from U.S. Pat. No. 5,045,560, Ex. No. 682 | 0.001 | 30 |
| according to the invention, Ex. No. 130 | 0.001 | 100 |

EXAMPLE D

Spodoptera Test

Solvent: 7 parts by weight of dimethylformamide/P compound: acetone

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with cater- pillars of the owlet moth (*Spodoptera frugiperda*), while the leaves are still moist.

After the specified period of time, the destruction in % is determined. 100% means that all the caterpillars have been killed; 0% means that none of the caterpillars have been killed.

In this test, a superior activity compared with the prior art is shown, for example, by the following compounds of the preparation examples: (2).

EXAMPLE E

Pre-Emergence Test

Solvent: 7 parts by weight of acetone

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, a superior activity compared with the prior art is shown, for example, by the following compounds of the preparation examples: (1), (4), (53), (56), (58), (60).

TABLE E1

| | pre emergence test/greenhouse | | |
|---|---|---|---|
| Active Compound | g/ha | ZEA MAYS | DIGITARIA SANGUINALIS |
| Known from U.S. Pat. No. 4,985,063, Ex. No. 249 | 250 | 40 | 70 |
| according to the invention, Ex. No. 112 | 250 | 0 | 90 |

TABLE E1-continued pre emergence test/greenhouse

| Active Compound | g/ha | ZEA MAYS | DIGITARIA SANGUINALIS |
|---|---|---|---|

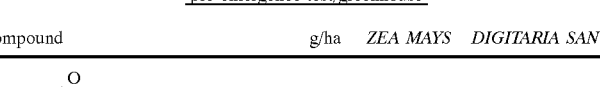

TABLE E2 pre emergence test/greenhouse

| Active Compound | g/ha | TRITICUM AESTIVUM | AGROPYRON REPENS | CYNODON DACTYLON | DIGITARIA SANGUINALIS |
|---|---|---|---|---|---|
| Known from U.S. Pat. No. 4,985,063, Ex. No. 243 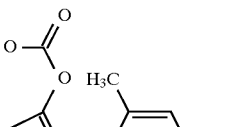 | 500 | 10 | 40 | 70 | 90 |
| according to the invention, Ex. No. 113 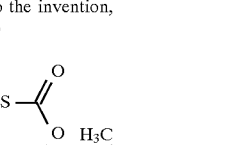 | 500 | 0 | 70 | 100 | 100 |

50

TABLE E3 pre emergence test/greenhouse

| Active Compound | g/ha | ALOPECURUS MYOSUROIDES | SETARIA VIRIDIS | SORGHUM HALEPENSE |
|---|---|---|---|---|
| Known from U.S. Pat. No. 4,985,063, Ex. No. 245 | 500 | 40 | 50 | 30 |

TABLE E3-continued pre emergence test/greenhouse

| Active Compound | g/ha | ALOPECURUS MYOSUROIDES | SETARIA VIRIDIS | SORGHUM HALEPENSE |
|---|---|---|---|---|
| [structure: ethyl carbonate ester of hexahydroindolizinone with 2,4,6-trimethylphenyl] according to the invention, Ex. No. 117 | 500 | 80 | 95 | 100 |
| [structure: ethyl thiocarbonate analog of hexahydroindolizinone with 2,4,6-trimethylphenyl] | | | | |

TABLE E4 pre emergence test/greenhouse

| Active Compound | g/ha | GLY-CINE MAX. | GOSSY-PIUM HIRSU-TUM | BROMUS SECAL-INUS | DIGI-TARIA SANGUIN-ALIS | ECHINO-CLOA CRUS-GALLI | PANI-CUM MILIA-CEUM | POLI-GONUM SPEC. | PORTU-LACA OLER-ACEA |
|---|---|---|---|---|---|---|---|---|---|
| Known from U.S. Pat. No. 5,045,560, Ex. No. 682 | 250 | 30 | 10 | 50 | 80 | 70 | 90 | 0 | 0 |
| [structure: isopropyl carbonate of N-cyclopentyl pyrrolinone with 2,4,6-trimethylphenyl] according to the invention, Ex. No. 130 | 250 | 0 | 0 | 80 | 100 | 100 | 100 | 70 | 100 |
| [structure: isopropyl thiocarbonate of N-cyclopentyl pyrrolinone with 2,4,6-trimethylphenyl] | | | | | | | | | |

TABLE E5

| | | pre emergence test/greenhouse | | | | | |
|---|---|---|---|---|---|---|---|
| Active Compound | g/ha | GLYCINE MAX. | DIGITARIA SANGUINALIS | ECHINOCLOA CRUS-GALLI | LOLIUM PERENNE | PANICUM MILIACEUM | SETARIA VIRIDIS |
| Known from U.S. Pat. No. 5,045,560, Ex. No. 578 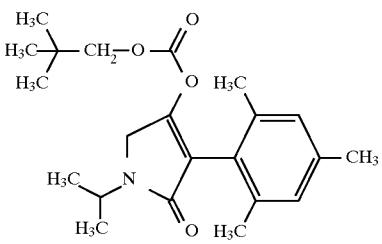 | 125 | 0 | 30 | 50 | 60 | 50 | 0 |
| according to the invention, Ex. No. 136 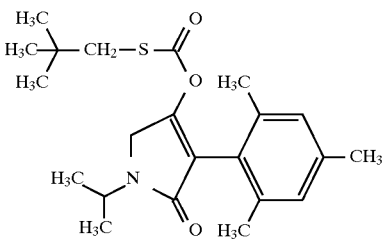 | 125 | 0 | 80 | 90 | 95 | 100 | 100 |

EXAMPLE F

Post-Emergence Test
Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 of water/ha. After three weeks, the degree of damage to the plants is rated in % damage in comparison to the development of the untreated control. The figures denote:

0%=no action (like untreated control)

100% =total destruction

In this test, a superior activity compared with the prior art is shown, for example, by the following compounds of the preparation examples: (1), (4), (53), (60), (85), (88).

TABLE F1

| | | pre emergence test/greenhouse | | | |
|---|---|---|---|---|---|
| Active Compound | g/ha | BROMUS SECALINUS | SETARIA VIRIDIS | IPOMOEA SPEC | SINAPIS ALBA |
| Known from U.S. Pat. No. 4,985,063, Ex. No. 249 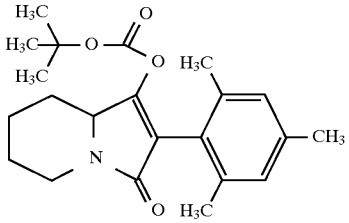 | 2000 | 0 | 80 | 0 | 10 |
| according to the invention, Ex. No. 112 | 2000 | 95 | 100 | 80 | 95 |

TABLE F1-continued pre emergence test/greenhouse

| Active Compound | g/ha | BROMUS SECALINUS | SETARIA VIRIDIS | IPOMOEA SPEC | SINAPIS ALBA |
|---|---|---|---|---|---|
| 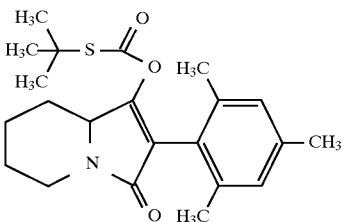 | | | | | |

TABLE F2 pre emergence test/greenhouse

| Active Compound | g/ha | TRITICUM AESTIVUM | GOSSYPIUM HIRSUTUM | ALOPECURUS MYOSUROIDES | CYNODON DACTYLON | LOLIUM PERENNE | SETARIA VIRIDIS | SORGHUM HALEPENSE |
|---|---|---|---|---|---|---|---|---|
| Known from U.S. Pat. No. 4,985,063 Ex. No. 243 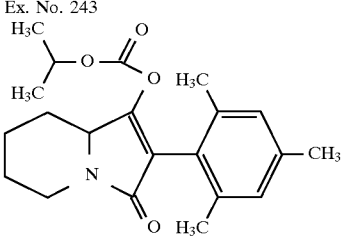 | 250 | 20 | 20 | 0 | 80 | 0 | 90 | 90 |
| according to the invention, Ex. No. 113 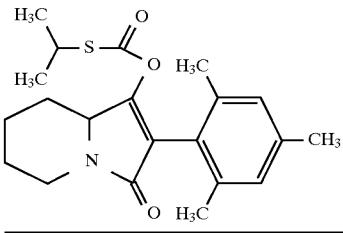 | 250 | 0 | 0 | 90 | 95 | 70 | 100 | 100 |

TABLE F3 pre emergence test/greenhouse

| Active Compound | g/ha | TRITICUM AESTIVUM | GLYCINE MAX. | DIGITARIA SANGUINALIS | SETARIA VIRIDIS | SORGHUM HALEPENSE |
|---|---|---|---|---|---|---|
| Known from U.S. Pat. No. 5,045,560 Ex. No. 578 | 250 | 10 | 10 | 80 | 80 | 70 |

TABLE F3-continued pre emergence test/greenhouse

| Active Compound | g/ha | TRITICUM AESTIVUM | GLYCINE MAX. | DIGITARIA SANGUINALIS | SETARIA VIRIDIS | SORGHUM HALEPENSE |
|---|---|---|---|---|---|---|
| 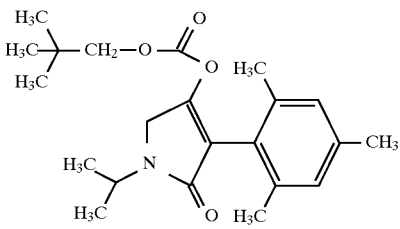 according to the invention, Ex. No. 136 | 250 | 0 | 0 | 95 | 90 | 90 |
| 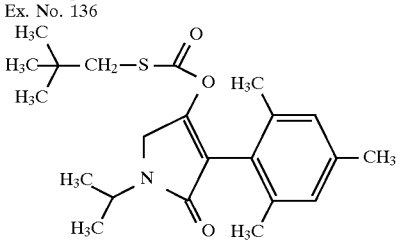 | | | | | | |

EXAMPLE G

Tetranychus Test (OP-resistant)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water containing emulsifier to the desired concentration.

Bean plants (*Phaseolus vulgaris*) which are heavily infested with the common red spider mite or two-spotted spider mite (*Tetranychus urticae*) in all stages of development are treated by being dipped into the preparation of the active compound of the desired concentration.

After the desired time, the mortality in % is determined. 100% means that all spider mites have been killed; 0% means that no spider mites have been killed.

In this test, the following compounds show a superior activity compared to the prior art:

TABLE G1

Tetranychus test (OP-resistant)

| Active Compound | Active Compound Concentration in % | Mortality in % after 7 days |
|---|---|---|
| Known from U.S. Pat. No. 4,985,063, Ex. No. 243 | 0.01 | 90 |
| | 0.001 | 80 |
| 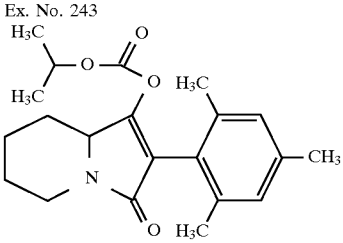 | | |

TABLE G1-continued

Tetranychus test (OP-resistant)

| Active Compound | Active Compound Concentration in % | Mortality in % after 7 days |
|---|---|---|
| 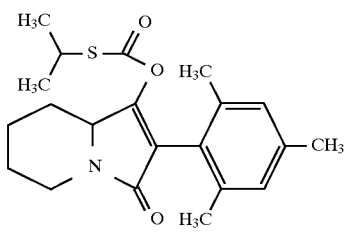 according to the invention, Ex. No. 113 | 0.01 | 95 |
| | 0.001 | 95 |

TABLE G2

Tetranychus test (OP-resistant)

| Active Compound | Active Compound Concentration in % | Mortality in % after 2 days |
|---|---|---|
| Known from U.S. Pat. No. 4,985,063, Ex. No. 252 | 0.01 | 40 |

TABLE G2-continued

Tetranychus test (OP-resistant)

| Active Compound | Active Compound Concentration in % | Mortality in % after 2 days |
|---|---|---|
| [structure: H3C-C(CH3)2-CH2-O-C(=O)-O- attached to piperidine-fused pyrrolinone with 2,4,6-trimethylphenyl] | | |
| [structure: H3C-C(CH3)2-CH2-S-C(=O)-O- attached to piperidine-fused pyrrolinone with 2,4,6-trimethylphenyl] according to the invention, Ex. No. 116 | 0.01 | 98 |

TABLE G3

Tetranychus test (OP-resistant)

| Active Compound | Active Compound Concentration in % | Mortality in % after 7 days |
|---|---|---|
| Known from U.S. Pat. No. 4,985,063, Ex. No. 245 [structure: H5C2-CH(CH3)-O-C(=O)-O- attached to piperidine-fused pyrrolinone with 2,4,6-trimethylphenyl] | 0.0001 | 70 |
| [structure: H5C2-CH(CH3)-S-C(=O)-O- attached to piperidine-fused pyrrolinone with 2,4,6-trimethylphenyl] according to the invention, Ex. No. 117 | 0.0001 | 95 |

TABLE G4

Tetranychus test (OP-resistant)

| Active Compound | Active Compound Concentration in % | Mortality in % after 7 days |
|---|---|---|
| Known from U.S. 5,045,560 Ex. No. 682 [structure: (H3C)2CH-O-C(=O)-O- attached to N-cyclopentyl pyrrolinone with 2,4,6-trimethylphenyl] | 0.001 | 60 |
| [structure: (H3C)2CH-S-C(=O)-O- attached to N-cyclopentyl pyrrolinone with 2,4,6-trimethylphenyl] according to the invention, Ex. No. 130 | 0.001 | 98 |

TABLE G5

Tetranychus test (OP-resistant)

| Active compound | Active compound Concentration in % | Mortality in % after 7 days |
| --- | --- | --- |
| Known from U.S. 5,045,560 Ex. No. 578 | 0.001 | 35 |
| 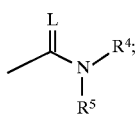 | 0.001 | 90 |
| 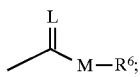 according to the invention, Ex. No. 136 | | |

What is claimed is:

1. A 3-arylpyrrolidine-2,4-dione derivative of the formula (I):

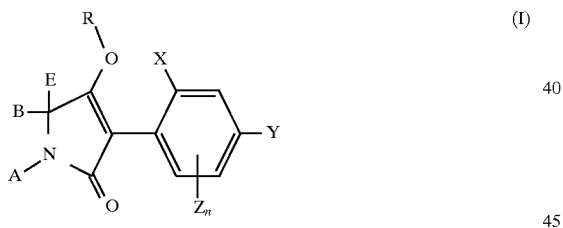

in which

A and B together with the nitrogen or carbon atom to which they are bonded, form a 4–8 membered cyclic ring wherein A and B together represent —(CH$_2$)—$_{2-6}$ which is uninterrupted or interrupted by a sulfur atom or a sulfoxide or a sulfonyl group;

E represents hydrogen, alkyl or alkoxyalkyl;

X represents alkyl, halogen or alkoxy;

Y represents hydrogen, alkyl, halogen, alkoxy or halogenoalkyl;

Z represents alkyl, halogen or alkoxy;

n represents a number from 0–3;

R represents one of the groups:

—SO$_2$—R$^3$;   (b)

-continued

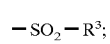

in which

L represents oxygen or sulfur in the case of group (a) or (c); or, in the case of group (d), one of L and M represents oxygen and the other represents sulfur or both L and M represent sulfur;

R$^1$, R$^2$ and R$^3$ independently of one another represent alkyl, alkoxy, alkylamino, dialkylamino, alkylthio, alkenylthio, alkynylthio or cycloalkylthio, each of which is unsubstituted or substituted by halogen, or represent phenyl, benzyl, phenoxy or phenylthio, each of which is unsubstituted or substituted by halogen, nitro, cyano, alkoxy, halogenoalkoxy, alkylthio, halogenoalkylthio, alkyl or halogenoalkyl;

R$^4$ and R$^5$ independently of one another represent hydrogen, or represent alkyl, alkenyl, alkoxy or alkoxyalkyl, each of which is unsubstituted or substituted by halogen, or represent phenyl or benzyl, each of which is unsubstituted or substituted by halogen, halogenoalkyl, alkyl or alkoxy; or R$^4$ and R$^5$ together represent an alkylene radical which is uninterrupted or interrupted by oxygen;

R$^6$ represents alkyl which is unsubstituted or substituted by halogen and which is uninterrupted or interrupted by oxygen, or represents phenyl which is unsubstituted or substituted by halogen, halogenoalkyl or alkoxy, or represents benzyl which is unsubstituted or substituted by halogen, halogenoalkyl, alkyl or alkoxy, or represents alkenyl or alkynyl;

or a pure enantiomeric form thereof.

2. The 3-aryl pyrrolidine-2,4-dione derivative of the formula (I) according to claim 1, in which E represent hydrogen or straight-chain or branched $C_1-C_{12}$-alkyl or $C_1-C_8$-alkoxyalkyl X represents $C_1-C_6$-alkyl, halogen or $C_1-C_6$-alkoxy, Y represents hydrogen, $C_1-C_6$-alkyl, halogen, $C_1-C_6$-alkoxy or $C_1-C_3$-halogenoalkyl, Z represents $C_1-C_6$-alkyl, halogen or $C_1-C_6$-alkoxy, $R^1$, $R^2$ and $R^3$ independently of one another represent $C_1-C_8$-alkyl, $C_1-C_8$-alkoxy, $C_1-C_8$-alkylamino, di-($C_1-C_8$)-alkylamino, $C_1-C_8$-alkylthio, $C_2-C_5$-alkenylthio, $C_2-C_5$-alkinylthio or $C_3-C_7$-cycloalkylthio, each of which is optionally substituted by halogen, or represent phenyl, benzyl, phenoxy or phenylthio, each of which is optionally substituted by halogen, nitro, cyano, $C_1-C_4$-alkoxy, $C_1-C_4$-halogenoalkoxy, $C_1-C_4$-alkylthio, $C_1-C_4$-halogenoalkylthio, $C_1-C_4$-alkyl or $C_1-C_4$-halogenoalkyl, $R^4$ and $R^5$ independently of one another represent $C_1-C_{20}$-alkyl, $C_1-C_{20}$-alkoxy, $C_2-C_8$-alkenyl or $C_1-C_{20}$-alkoxy-$C_1-C_{20}$-alkyl, each of which is optionally substituted by halogen, or represent phenyl which is optionally substituted by halogen, $C_1-C_{20}$-halogenoalkyl, $C_1-C_{20}$-alkyl or $C_1-C_{20}$-alkoxy, or represent benzyl which is optionally substituted by halogen, $C_1-C_{20}$-alkyl, $C_1-C_{20}$-halogenoalkyl or $C_1-C_{20}$-alkoxy, or together represent a $C_2-C_6$-alkylene ring which is optionally interrupted by oxygen, $R^6$ represents $C_1-C_{20}$-alkyl which is optionally substituted by halogen and which can be interrupted by oxygen, or represents phenyl which is optionally substituted by halogen, $C_1-C_{20}$-halogenoalkyl or $C_1-C_{20}$-alkoxy, or represents benzyl which is optionally substituted by halogen, $C_1-C_{20}$-halogenoalkyl or $C_1-C_{20}$-alkoxy, or represents $C_2-C_8$-alkenyl, or represents $C_2-C_5$-alkinyl, or a pure enantiomeric form thereof.

3. The 3-arylpyrrolidine-2,4-dione derivative of the formula (I) according to claim 1, in which A and B together with the nitrogen or carbon atom to which they are bonded form a 4 to 7-membered cyclic ring which can be interrupted by a sulphur atom, or by a sulphoxide or sulphonyl group, E represents hydrogen or straight-chain or branched $C_1-C_{10}$-alkyl or $C_1-C_6$-alkoxyalkyl, X represents $C_1-C_4$-alkyl, halogen or $C_1-C_4$-alkoxy, Y represents hydrogen, $C_1-C_6$-alkyl, halogen, $C_1-C_4$-alkoxy or $C_1-C_2$-halogenoalkyl, Z represents $C_1-C_4$-alkyl, halogen or $C_1-C_4$-alkoxy, $R^1$, $R^2$ and $R^3$ independently of one another represent $C_1-C_6$-alkyl, $C_1-C_6$-alkoxy, $C_1-C_6$-alkylamino, di-($C_1-C_6$)-alkylamino, $C_1-C_6$-alkylthio, $C_3-C_4$-alkenylthio, $C_2-C_4$-alkinylthio or $C_3-C_6$-cycloalkylthio, each of which is optionally substituted by halogen, or represent phenyl, benzyl, phenoxy or phenylthio, each of which is optionally substituted by fluorine, chlorine, bromine, nitro, cyano, $C_1-C_3$-alkoxy, $C_1-C_3$-halogen-alkoxy, $C_1-C_3$-alkylthio, $C_1-C_3$-halogenoalkylthio, $C_1-C_3$-alkyl or $C_1-C_3$halogenoalkyl, $R^4$ and $R^5$ independently of one another represent $C_1-C_{20}$-alkyl, $C_1-C_{20}$-alkoxy, $C_2-C_8$-alkenyl or $C_1-C_{20}$-alkoxy-$C_1-C_{20}$-alkyl, each of which is optionally substituted by halogen, or represent phenyl which is optionally substituted by halogen, $C_1-C_5$-halogenoalkyl, $C_1-C_5$-alkyl or $C_1-C_5$-alkoxy, or represent benzyl which is optionally substituted by halogen, $C_1-C_5$-alkyl, $C_1-C_5$-halogenoalkyl or $C_1-C_5$-alkoxy, $R^6$ represents $C_1-C_{20}$-alkyl which is optionally substituted by halogen and which can be interrupted by oxygen, or represents phenyl which is optionally substituted by halogen, $C_1-C_5$-halogenoalkyl or $C_1-C_5$-alkoxy, or represents benzyl which is optionally substituted by halogen, $C_1-C_5$-halogenoalkyl or $C_1-C_5$-alkoxy, or a pure enantiomeric form thereof.

4. A 3-arylpyrrolidine-2,4-dione derivative of the formula (I) according to claim 1, in which A and B together with the nitrogen or carbon atom to which they are bonded form a 5-6-membered cyclic ring which can be interrupted by a sulphur atom or by a sulphoxide or sulphonyl group, E represents hydrogen or straight-chain or branched $C_1-C_8$-alkyl or $C_1-C_4$-alkoxyalkyl, X represents methyl, ethyl, propyl, i-propyl, fluorine, chlorine, bromine, methoxy or ethoxy, Y represents hydrogen, methyl, ethyl, propyl, i-propyl, butyl, i-butyl, tert.-butyl, fluorine, chlorine, bromine, methoxy, ethoxy or trifluoromethyl, Z represents methyl, ethyl, i-propyl, butyl, i-butyl, tert.-butyl, fluorine, chlorine, bromine, methoxy or ethoxy, $R^1$, $R^2$ and $R^3$ independently of one another represent $C_1-C_4$-alkyl, $C_1-C_4$-alkoxy, $C_1-C_4$-alkylamino, di-($C_1-C_4$-alkyl)-amino or $C_1-C_4$-alkylthio, each of which is optionally substituted by fluorine or chlorine, or represent phenyl, benzyl, phenoxy or phenylthio, each of which is optionally substituted by fluorine, chlorine, bromine, nitro, cyano, $C_1-C_2$-alkoxy, $C_1-C_4$-fluoroalkoxy, $C_1-C_2$-chloroalkoxy, $C_1-C_2$-alkylthio, $C_1-C_2$-fluoroalkylthio, $C_1-C_2$-chloroalkylthio or $C_1-C_3$-alkyl, $R^4$ and $R^5$ independently of one another represent each of which is optionally substituted by fluorine, chlorine, bromine, $C_1-C_{20}$-alkyl, $C_1-C_{20}$-alkoxy, $C_2-C_8$-alkenyl or $C_1-C_{20}$-alkoxy-($C_1-C_{20}$)alkyl, or represent phenyl which is optionally substituted by fluorine, chlorine, bromine, $C_1-C_{20}$-halogenoalkyl, $C_1-C_{20}$-alkyl or $C_1-C_{20}$-alkoxy, or represent benzyl which is optionally substituted by fluorine, chlorine, bromine, $C_1-C_4$-alkyl, $C_1-C_4$-halogenoalkyl or $C_1-C_4$-alkoxy, $R^6$ represents $C_1-C_{20}$-alkyl which is optionally substituted by fluorine, chlorine or bromine and which can be interrupted by oxygen, or represents phenyl which is optionally substituted by fluorine, chlorine, bromine, $C_1-C_4$-halogenoalkyl or $C_1-C_4$-alkoxy, or represents benzyl which is optionally substituted by fluorine, chlorine, bromine, $C_1-C_4$-halogenoalkyl or $C_1-C_4$-alkoxy, or a pure enantiomeric form thereof.

5. The 3-arylpyrrolidine-2,4-dione derivative according to claim 1, having the formula

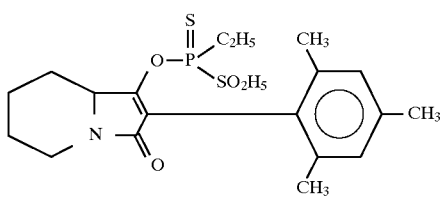

6. The 3-arylpyrrolidine-2,4-dione derivative according to claim 1, having the formula

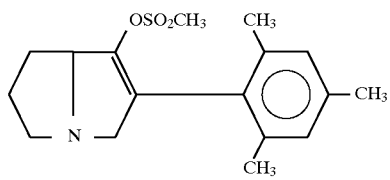

7. The 3-arylpyrrolidine-2,4-dione derivative according to claim 1, having the formula

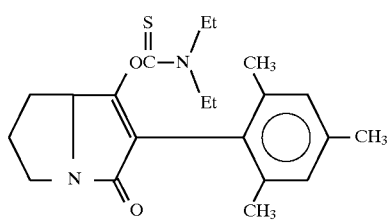

8. The 3-arylpyrrolidine-2,4-dione derivative according to claim 1, having the formula

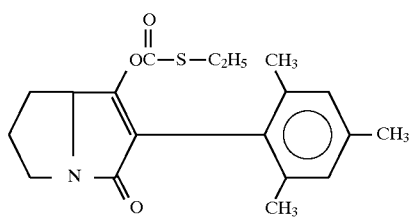

9. The 3-arylpyrrolidine-2,4-dione derivative according to claim 1, having the formula

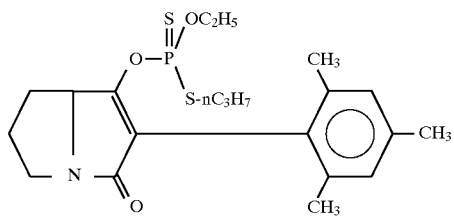

10. An insecticidal composition comprising an insecticidally effective amount of a 3-arylpyrrolidine-2,4-dione derivative according to claim 1 and a carrier.

11. An acaricidal composition comprising an acaricidally effective amount of a 3-arylpyrrolidine-2,4-dione derivative according to claim 1 and a carrier.

12. A herbidial composition comprising a herbicidally effective amount of a 3-arylpyrrolidine-2,4-dione derivative according to claim 1 and a carrier.

13. A method of combating insects comprising applying to the weeds or their environment an insecticidally effective amount of a 3-arylpyrrolidine-2,4-dione derivative according to claim 1.

14. The method according to claim 13, wherein the 3-arylpyrrolidine-2,4-dione derivative is selected from the group consisting of

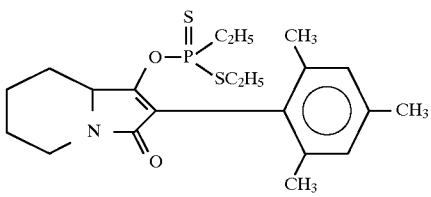

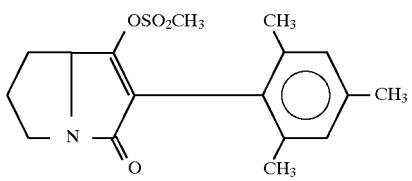

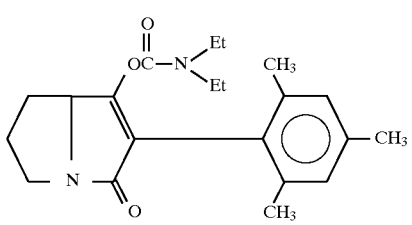

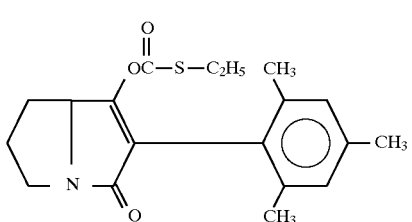

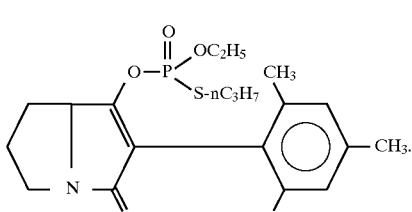

15. A method of combating acarides comprising applying to the acarides or their environment an acaricidally effective amount of a 3-arylpyrrolidine-2,4-dione derivative according to claim 1.

16. The method according to claim 15, wherein the 3-arylpyrrolidine-2,4-dione derivative is selected from the group consisting of

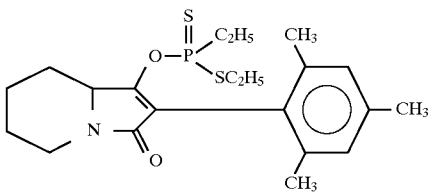

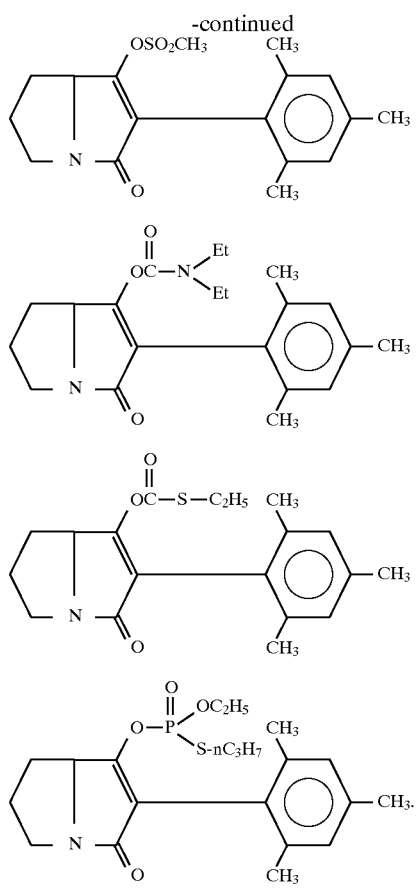

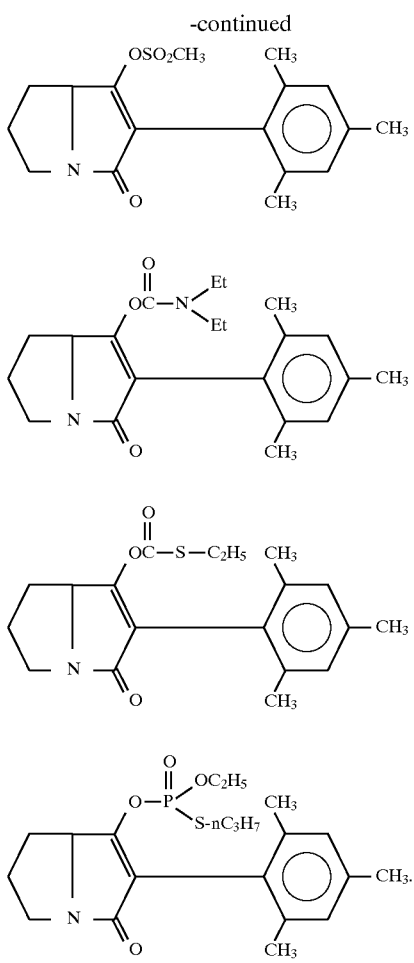

17. A method of combating weeds comprising applying to the weeds or their environment a herbicidally effective amount of a 3-arylpyrrolidine-2,4-dione derivative according to claim 1.

18. The method according to claim 17, wherein the 3-arylpyrrolidine-2,4-dione derivative is selected from the group consisting of

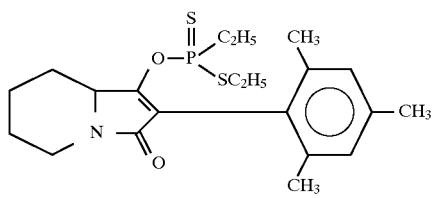

19. The 3-arylpyrrolidine-2,4-dione derivative according to claim 1, wherein A and B together represent —(CH$_2$)$_3$— or —(CH$_2$)$_4$—.

20. The 3-arylpyrrolidine-2,4-dione derivative according to claim 1, wherein A and B together represent an uninterrupted 4-8 membered cyclic ring.

* * * * *